(12) United States Patent
Ghalili et al.

(10) Patent No.: US 12,109,381 B2
(45) Date of Patent: Oct. 8, 2024

(54) CANNABINOID AND MENTHOL TRANSDERMAL DELIVERY SYSTEMS AND METHODS

(71) Applicants: Babak Ghalili, New York, NY (US); John Borja, Keyport, NJ (US); Arthur Goldberg, Livingston, NJ (US)

(72) Inventors: Babak Ghalili, New York, NY (US); John Borja, Keyport, NJ (US); Arthur Goldberg, Livingston, NJ (US)

(*) Notice: Subject to any disclaimer, the term of this patent is extended or adjusted under 35 U.S.C. 154(b) by 118 days.

(21) Appl. No.: 17/412,442

(22) Filed: Aug. 26, 2021

(65) Prior Publication Data
US 2022/0062603 A1 Mar. 3, 2022

Related U.S. Application Data

(60) Provisional application No. 63/070,554, filed on Aug. 26, 2020.

(51) Int. Cl.
| | | |
|---|---|---|
| *A61M 37/00* | (2006.01) | |
| *A61K 9/70* | (2006.01) | |
| *A61K 31/045* | (2006.01) | |
| *A61K 45/06* | (2006.01) | |
| *A61K 47/14* | (2017.01) | |
| *A61K 47/20* | (2006.01) | |

(52) U.S. Cl.
CPC ........... *A61M 37/00* (2013.01); *A61K 9/7023* (2013.01); *A61K 31/045* (2013.01); *A61K 45/06* (2013.01); *A61K 47/14* (2013.01); *A61K 47/20* (2013.01); *A61K 9/7084* (2013.01); *A61M 2037/0007* (2013.01); *A61M 2205/0233* (2013.01); *A61M 2205/055* (2013.01)

(58) Field of Classification Search
CPC .......... A61M 37/00; A61M 2037/0007; A61M 2205/0233; A61M 2205/055; A61K 9/7023; A61K 31/045; A61K 45/06; A61K 47/14; A61K 47/20; A61K 9/7084; A61K 9/7061; A61K 31/05; A61K 31/352; A61K 47/12; A61P 1/00
See application file for complete search history.

(56) References Cited

U.S. PATENT DOCUMENTS

| | | | |
|---|---|---|---|
| 5,869,087 A | 2/1999 | Hirano et al. | |
| 5,882,677 A | 3/1999 | Kupperblatt | |
| 6,275,728 B1 | 8/2001 | Venkatraman et al. | |
| 6,495,097 B1 | 12/2002 | Streit et al. | |
| 9,839,693 B2 | 12/2017 | Borja et al. | |
| 10,842,758 B1 * | 11/2020 | Fitzsimmons | ......... A61K 47/10 |
| 2002/0161323 A1 | 10/2002 | Miller et al. | |
| 2012/0201891 A1 | 8/2012 | Cottrell et al. | |
| 2013/0281523 A1 | 10/2013 | Letendre et al. | |
| 2016/0184212 A1 | 6/2016 | Casasanta et al. | |
| 2018/0344676 A1 * | 12/2018 | Hoag | ................... A61K 36/185 |
| 2018/0344860 A1 | 12/2018 | Naheed | |
| 2019/0110981 A1 | 4/2019 | Weimann | |
| 2019/0216745 A1 | 7/2019 | Song | |
| 2019/0231711 A1 | 8/2019 | Weimann | |
| 2019/0247299 A1 | 8/2019 | Cameron et al. | |
| 2020/0069605 A1 * | 3/2020 | Ghalili | ..................... A61K 9/02 |
| 2020/0069606 A1 | 3/2020 | Ghalili | |
| 2020/0214996 A1 | 7/2020 | Ghalili | |
| 2021/0236436 A1 * | 8/2021 | Goldberg | ............ A23L 27/2028 |

FOREIGN PATENT DOCUMENTS

| | | | | |
|---|---|---|---|---|
| WO | 2008024408 A2 | 2/2008 | | |
| WO | WO-2019002154 A1 * | 1/2019 | ........... | A61K 9/0009 |
| WO | WO-2020263643 A1 * | 12/2020 | ........... | A61K 31/165 |

OTHER PUBLICATIONS

Malcolm. Methoderm: helping to manage that itch. Dermatological Nursing 2018 (Year: 2018).*
Liu et al. (Cyclodextrin Encapsulation to Prevent the Loss of I-Menthol and its Retention during Drying, Biosci. Biotechnol. Biochem., 2000) (Year: 2000).*
Wang et al., (Transdermal iontophoresis: combination strategies to improve transdermal iontophoretic drug delivery, European Journal of Pharmaceutics and Biopharmaceutics, 2005 (Year: 2005).*
"Humectants and Moisturizers: What's the Difference?" Skinbetter Science, Dec. 28, 2016, https://skinbetter.com/humectants-moisturizers-difference/, 6 pages.
"Undecylenic acid topical", Cardiology Associates of NNY, Sep. 8, 2017, http://www.cardiologynny.com/PatientPortal/MyPractice.aspx?UAID=%7B16300E1B-EC83-4B13-B3F3-SE33D932B385%7D&ID=HW5d03686a1&Title=Cruex#:~:text=Undeclyenic%20acid%20topical%20is%20used,listed%20in%20medication%20guide, 2 pages.
Al-Akayleh, "Therapeutic deep eutectic system for capric acid and menthol:Characterization and pharmaceutical application", Journal of Drug Delivery Science and Technology 53 (2019) 1-10, 10 pages.
Alankar, "A Review on Peppermint Oil", Asian Journal of Pharmaceutical and Clinical Research, vol. 2, Issue 2, Apr.-Jun. 2009, 7 pages.
Echo, "What is Full-Spectrum Hemp Oil and Why is it Important?" Published in Education, Overview of Cannabinoids, May 5, 2017, https://echoconnection.org/full-spectrum-hemp-oil-important/, 5 pages.
International Search Report and Written Opinion, United States Patent & Trademark Office, Application No. PCT/US2021/017527, mailed Jul. 16, 2021, 22 pages.

(Continued)

*Primary Examiner* — Robert A Wax
*Assistant Examiner* — John Seungjai Kwon
(74) *Attorney, Agent, or Firm* — Ziegler IP Law Group LLC.

(57) ABSTRACT

The present disclosure relates to compositions, methods of use and methods of manufacturing of transdermal delivery systems, patches, vehicles and devices including an iontophoretic transdermal delivery system, patch, vehicle or device used to relieve pain (i.e., analgesics) and/or inflammation that contain a pharmaceutically effective amount of a pharmaceutically acceptable and effective cannabinoid and menthol.

20 Claims, 12 Drawing Sheets

(56) References Cited

OTHER PUBLICATIONS

Krizek et al. "Menthol-based hydrophobic deep eutectic solvents; Towards greener and efficient extraction of phytocannabinoids" Journal of Cleaner Production, Available onling May 10, 2018, http://doi.org/10.1016/j.depro.2018.05.080, 6 pages.

Muzenda "Interactions of Polar and Nonpolar volatile organic compounds with methyl Ester solvents" 3rd International Conference on Medical Sciences and Chemical Engineering (ICMSCE'2013) Dec. 25-26, 2013 Bangkok (Thailand), 22-26.

Nunley, "What is Full-Spectrum Hemp Oil?" Medical Marijuana, Inc., Aug. 18, 2019, https://www.medicalmarijuanainc.com/full-spectrum-hemp-oil/, 13 pages.

Otto et al. "What is the future of heated transdermal delivery systems?" Therapeutic Delivery (2014) vol. 5, issue 9, https://www.future-science.com/doi/pdfplus/10.4155/tde.14.66, ISSN 2041-5990, 4 pages.

International Search Report, Application No. PCT/US21/47644, Mailed Feb. 7, 2022, 4 pages.

Written Opinion of The International Searching Authority, Application No. PCT/US21/47644, Mailed Feb. 7, 2022, 13 pages.

* cited by examiner

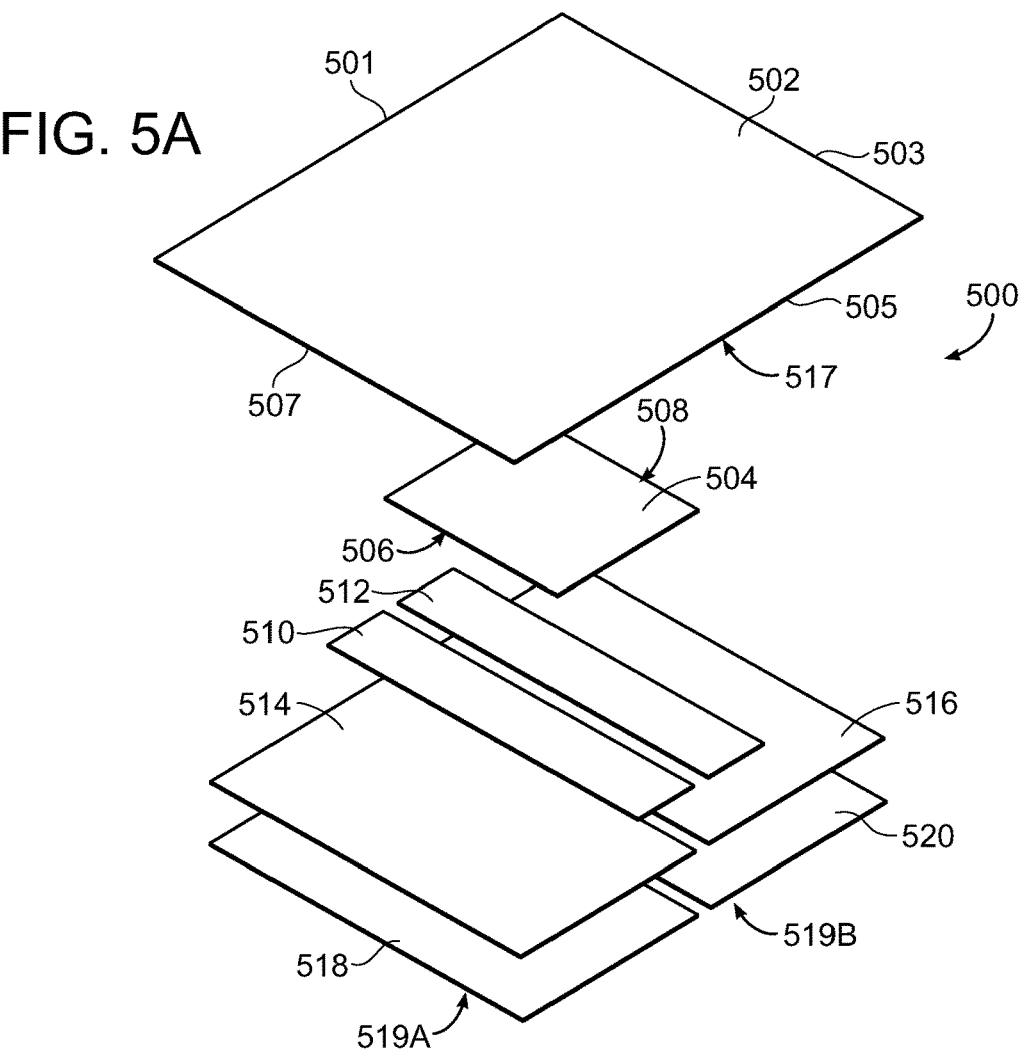
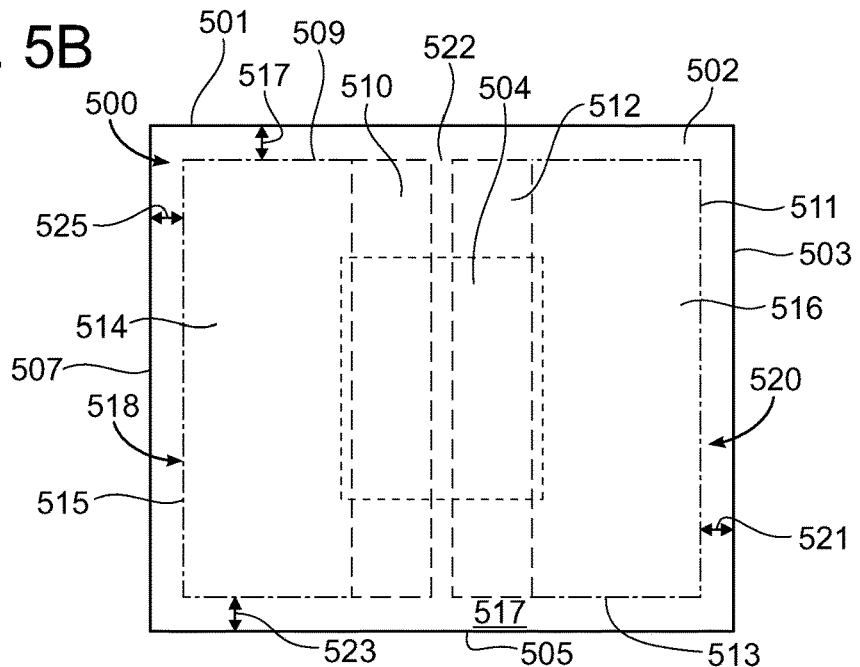

FIG. 6A
FIG. 6B
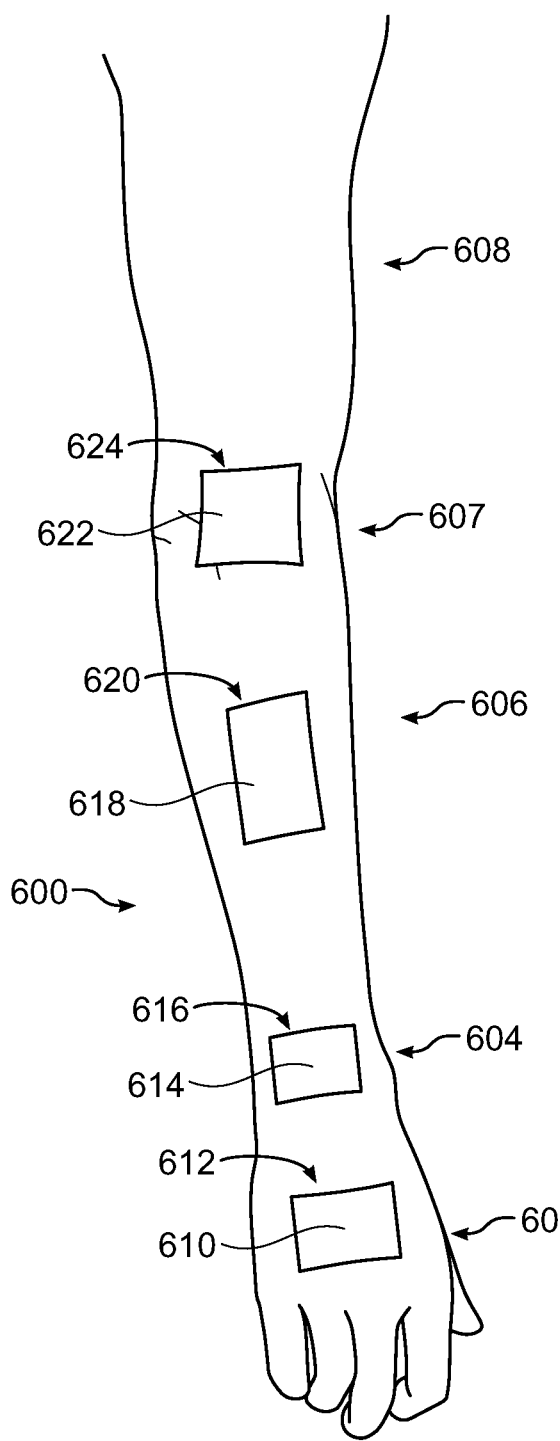
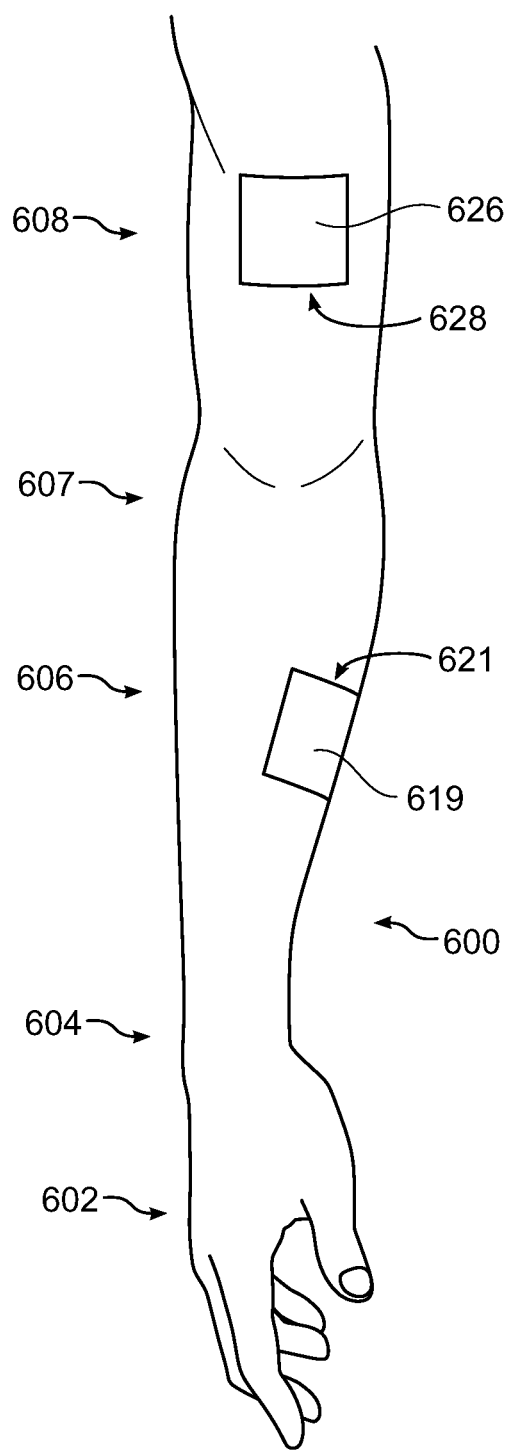

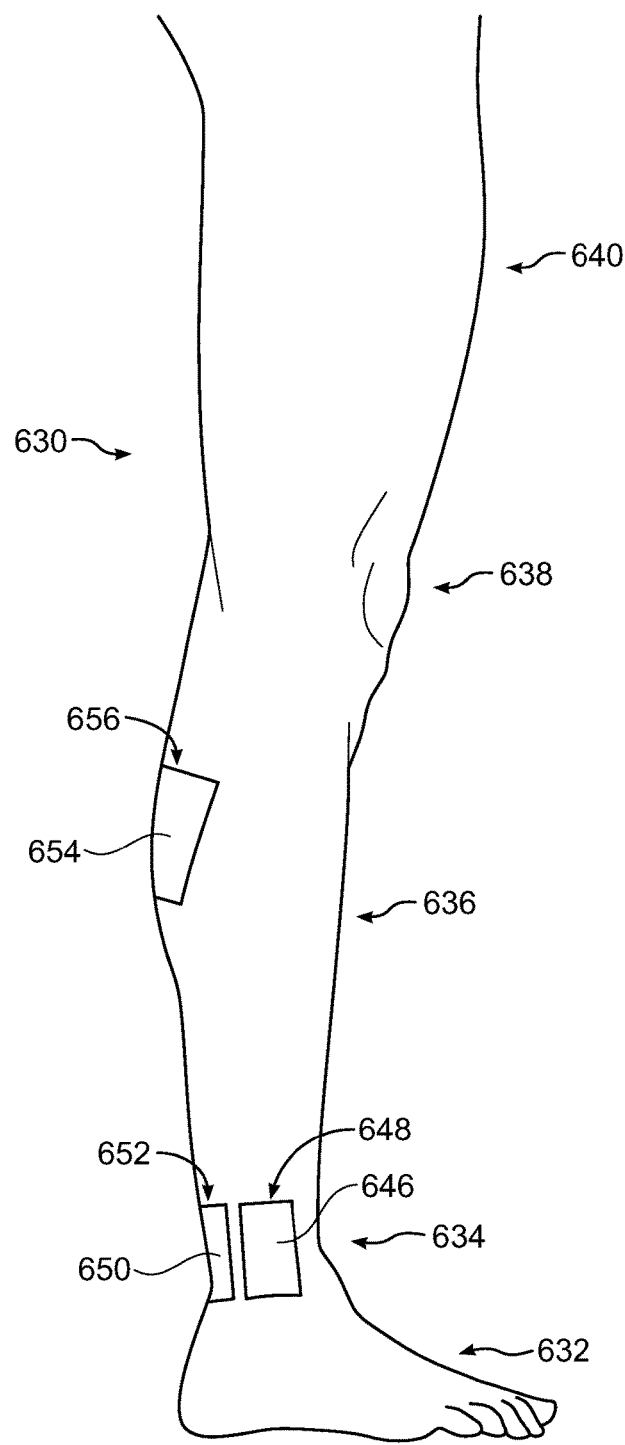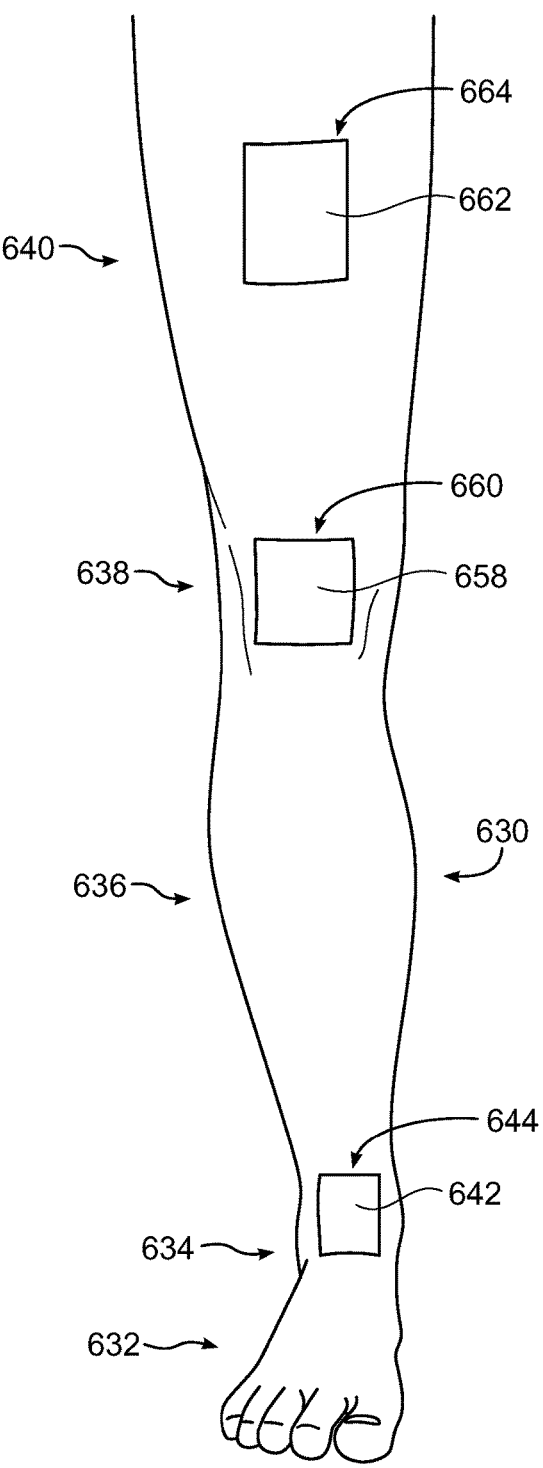

CANNABINOID AND MENTHOL TRANSDERMAL DELIVERY SYSTEMS AND METHODS

CROSS-REFERENCE TO RELATED APPLICATIONS

This application claims priority to and the benefit of U.S. Provisional Patent Application Ser. No. 63/070,554 filed Aug. 26, 2020, the disclosure of which is incorporated herein by reference in its entirety.

FIELD

The aspects of the present disclosure relate to transdermal delivery systems, patches, vehicles and devices as well as methods of making and using same including active agents such as cannabinoids and menthol.

BACKGROUND

There is a need for novel treatments for pain and inflammation on various parts of the body. Some current agents may be ineffective and can, for example, come with unacceptable side effects. Furthermore, there is a growing concern about the overuse of opioid pain treatments.

Topical delivery systems, patches, vehicles and devices have been used to deliver of active agents. However, many such delivery systems, patches, vehicles and devices can have shortcomings such as accelerating penetration of active ingredients.

It would be preferable to have a topical delivery system, vehicle and device that would provide a better and faster penetration of active ingredients so that the active ingredients are administered to a patient with improved speed.

BRIEF DESCRIPTION OF THE DRAWINGS

The accompanying drawings illustrate presently preferred embodiments of the present disclosure, and together with the general description given above and the detailed description given below, serve to explain the principles of the present disclosure.

FIGS. 5A and 5B illustrate an iontophoretic embodiment of the present disclosure;

FIGS. 6A to 6F illustrate an exemplary implementation of the aspects of the disclosed embodiments.

SUMMARY

Figure 1:
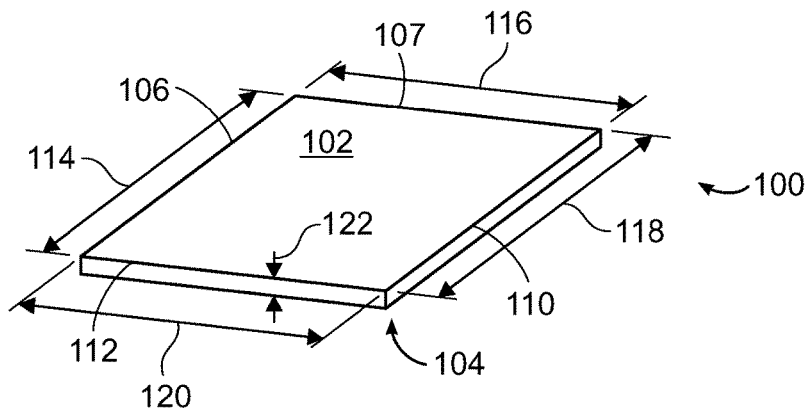
FIG. 1 is a perspective view of an embodiment of the present disclosure.

In one embodiment, a transdermal delivery system is provided. The transdermal delivery system includes a first hydrogel reservoir and a second hydrogel reservoir separated from each other one of the first hydrogel reservoir and the second hydrogel reservoir including an anionic or cationic surfactant, at least one cannabinoid and a stabilized menthol composition, the stabilized menthol composition including a pre-formed mixture of menthol and at least one menthol stabilizer compound including undecylenic acid methyl ester, undecylenic acid or a salt of undecylenic acid; and a circuit apparatus including a power source, the circuit apparatus configured to supply power to the first hydrogel reservoir and the second hydrogel reservoir.

In another embodiment, another transdermal delivery system is provided. The transdermal delivery system includes a first hydrogel reservoir and a second hydrogel reservoir separated from each other, one of the first hydrogel reservoir and the second hydrogel reservoir an anionic or cationic surfactant, including full spectrum hemp oil and a stabilized menthol composition, the stabilized menthol composition including a pre-formed mixture of menthol and at least one menthol stabilizer compound including undecylenic acid methyl ester, undecylenic acid or a salt of undecylenic acid; and a circuit apparatus including a power source, the circuit apparatus configured to supply power to the first hydrogel reservoir and the second hydrogel reservoir, wherein the transdermal delivery system includes less than 0.3% THC and the full spectrum hemp oil is purified to include the below stated amounts of one or more of the following impurities:

- less than 0.1 µg/kg of each of Aflatoxins BI, 82, G1, G2 and the sum of all positive Aflatoxins is less than 0.4 µg/kg;
- less than 0.1 mg/kg of each of Glufosinate, Glyphosate and Aminomethylphosphonic acid (AMPA);
- less than 0.02 mg/kg of mercury;
- less than 0.03 mg/kg of arsenic;
- less than 0.01 mg/kg of cadmium; and
- less than 0.05 mg/kg of lead.

In another embodiment, a method of treating pain or inflammation in a body part or portion thereof of a mammal using a transdermal delivery system is provided. The transdermal delivery system includes a first hydrogel reservoir and a second hydrogel reservoir separated from each other, one of the first hydrogel reservoir and the second hydrogel reservoir including an anionic or cationic surfactant, at least one cannabinoid and a stabilized menthol composition, the stabilized menthol composition including a pre-formed mixture of menthol and at least one menthol stabilizer compound including undecylenic acid methyl ester, undecylenic acid or a salt of undecylenic acid; and a circuit apparatus including a power source, the circuit apparatus configured to supply power to the first hydrogel reservoir and the second hydrogel reservoir. The method includes topically applying the said first hydrogel reservoir and said second hydrogel reservoir to a skin surface of the body part of the mammal and thereby completing an electrical circuit through the skin of the mammal between said first hydrogel reservoir and said second hydrogel reservoir using said power source.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by embodiments of the present disclosure. As used herein, "about" may be understood by persons of ordinary skill in the art and can vary to some extent depending upon the context in which it is used. If there are uses of the term which are not clear to persons of ordinary skill in the art, given the context in which it is used, "about" may mean up to plus or minus 10% of the particular term.

The terms "%", "% by weight", "weight %" and "wt %" are all intended to mean unless otherwise stated, percents by weight based upon a total weight of 100% end composition weight. Thus 10% by weight means that the component constitutes 10 wt. parts out of every 100 wt. parts of total composition.

The term "pharmaceutically acceptable" means that which is useful in preparing a pharmaceutical composition that is generally non-toxic and is not biologically undesirable and includes that which is acceptable for veterinary use and/or human pharmaceutical use.

The term "topically acceptable" means the compound, substance or device may be administered to or onto the surface of a patient, including the skin or other accessible tissues, without substantial harmful effects to the body part and/or its surfaces.

The terms "treating" and "effective amount", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neoadjuvant treatment of a subject.

All of the embodiments included here are with the proviso that the sum of ingredients in the exemplary compositions does not exceed 100%.

The delivery systems, patches, vehicles and devices of the present disclosure are also useful in the fields of human medicine for the administration of active agents to people (i.e., human patients) and veterinary medicine for the administration of active agents to pets and farm animals.

The aspects of the present disclosure relate to transdermal delivery systems, patches, vehicles and devices used to relieve pain (i.e., analgesics) and/or inflammation, methods of making such transdermal delivery systems, patches, vehicles and devices and methods of using such transdermal delivery systems, patches, vehicles and devices including topically applied (e.g., to skin or another body part) such transdermal delivery systems, patches, vehicles and devices including pharmaceutical transdermal delivery systems, patches, vehicles and devices, including analgesic and/or anti-inflammatory pharmaceutical compositions for the treatment of pain and/or inflammation, that contain a pharmaceutically effective amount of a pharmaceutically acceptable and effective cannabinoid and menthol. Such transdermal delivery systems, patches, vehicles and devices of the present disclosure can include, for example, gel material (e.g., hydrogel material) alone or in combination with a backing material as well as iontophoretic delivery systems, patches, vehicles and devices that include gel material (e.g., hydrogel material including a hydrogel reservoir) with additional electrical components and use electrical energy to aid in the penetration and administration of active agents contained therein.

The combination of cannabinoid and menthol into a single therapeutic composition, for example, a transdermal delivery system, patch, vehicle or device can provide improved and better focused delivery of the actives to a patient than separately applying the cannabinoid and menthol separately (to different areas of the body or layered one on top of another) without the hydrous or other hydrogel vehicles (e.g., hydrogel reservoir).

Transdermal delivery systems, patches, vehicles and devices, such as, for example, embodiments of the present disclosure, include transdermal delivery systems, patches, vehicles and devices in a desired size, shape and weight which, in the ordinary course of usage, can be placed topically on a body part (e.g., arm, leg, knee, torso, head, neck, foot as well as those parts that make-up them) for purposes of local and/or systemic administration of particular therapeutic agents for a time sufficient to be effective for purposes of therapeutic activity to the body part and tissues thereof or other tissues remote from the application site in order to provide relief from the malady being suffered (e.g., pain relief though an analgesic and/or anesthetic effect) including a malady of the body part (e.g., pain and/or inflammation) to which the transdermal delivery systems, patches, vehicles and devices of the present disclosure can be directly applied for relief. After being present in contact with the body part for a time sufficient to be effective for purposes of therapeutic activity, they can be removed from the body part. Such application to the body part includes placing the transdermal delivery systems, patches, vehicles and devices in contact with the skin covering the body part.

Embodiments of the present disclosure may be delivered for local or systemic administration to a body part of a person to be treated with the embodiment, for example, a body or skin surface thereof by placing an embodiment of the present disclosure on a body part or skin surface thereof, for example, a knee, leg, back of hand, arm, lower back, upper back, shoulder and forehead, in active agent-transmitting relation thereto, the active agents being cannabinoid, for example, a phytocannabinoid or full spectrum hemp oil, and menthol. Alternatively, an embodiment of the present disclosure may be incorporated into a transdermal delivery system, patch, vehicle or device, such as a unit dose delivery transdermal delivery system, patch, vehicle or device.

Non-limiting examples of injuries or other physical diseases or conditions causing pain and/or inflammation for which embodiments of the present disclosure can be used to reduce or lessen the pain and/or inflammation can include arthritis conditions (e.g., osteo, rheumatoid, psoriatic, fibromyalgia, etc.), head pain (e.g., concussion, head ache, migraine), orthopedic injuries or conditions (e.g., bone fracture or break; dislocated joint or bone; torn, stressed or strained ligament or tendon; bruising or trauma to tissue; back or spinal pain or herniated disc; tendonitis; gout, bursitis), muscles aches and pains (e.g., from stress and physical exertion) and post-surgery recovery (e.g., recovery from orthopedic surgery to repair a broken bone, back condition such as herniated disk or torn ligament, orthoscopic surgery).

Embodiments of the present disclosure include treated hydrogel material of the present disclosure including cannabinoids and menthol alone, with a backing material or as iontophoretic delivery systems, patches, vehicles and devices that include gel material (e.g., hydrogel material also referred to herein as a hydrogel reservoir) with additional electrical components of the present disclosure.

Cannabinoids included in embodiments of the present disclosure are an active agent and a class of chemical compounds that can be derived from plants (phytocannabinoids) or synthetically produced. Cannabinoids can have local and systemic analgesic, pain relieving, pain treating and anti-inflammatory therapeutic properties. Cannabinoids may also have other medical benefits and/or be useful in treating other medical conditions including, for example, reduction of anxiety and depression, reduction of symptoms like nausea, vomiting and pain related to cancer treatments, reduction of acne, protection of the neural system and benefits for the heart and circulatory system by the lowering of blood pressure. Cannabinoids can also have therapeutic value as a nutrient and can be included in composition and method embodiments of the present disclosure in an effective amount to perform that function.

Examples of phytocannabinoids include Cannabidiol (CBD) including, for example, CBD oil, Cannabinol (CBN), Cannabigerol (CBG) and tetrahydrocannabinol (THC), the latter being a known psychotropic compound and the first two being non-psychotropic. *Cannabis* and hemp plants can exhibit wide variation in the quantity and type of cannabinoids they produce. Selective breeding of the plants can be used to control the genetics of plants and modify the cannabinoids produced by the plant. For example, there are strains that are used as fiber (commonly called hemp) and, as a result, have been bred such that they are low in psychoactive chemicals like THC. Such strains (e.g., hemp) used in medicine are, for example, often bred for high CBD content and have minimal levels of THC (less than 0.3%). Some embodiments of the present disclosure include a cannabinoid component with less than 0.3% THC and may also include embodiments that do not include controlled substances as defined in the Controlled Substances Act. Examples of topical, transdermal and/or pharmaceutically effective cannabinoids include CBD (for example, full spectrum hemp oil). Cannabinoid, including, for example, phytocannabinoids including CBD, can be in an amount of about 25 wt % to about 65 wt %, about 35 wt % (based on 25% CBD conc. in CBD or hemp oil). CBD can be in an amount of about 25 wt % to about 65 wt %, about 35 wt % (wt % based on the hydrogel weight). Full spectrum CBD or hemp oil can be in an amount of about 25 wt % to about 65 wt %, about 35 wt % (based on 25% CBD conc. in the CBD or hemp oil) (wt % based on the hydrogel weight). Unit dosage formulations of the embodiments of the present disclosure can include cannabinoid, for example, a phytocannabinoid (including for example, CBD) in the amount of about 5.0 mg. to about 5000.00 mg. (based on 25% CBD conc. in the CBD or hemp oil). Unit dosage formulations of the embodiments of the present disclosure can include CBD in the amount of about 1.250 mg. to about 1250.00 mg. Unit doses of full spectrum CBD or hemp oil can include an amount of about 5.0 mg. to about 5000.00 mg. (based on 25% CBD conc. in the CBD or hemp oil). Unit dosage formulations of the embodiments of the present disclosure can include cannabinoid, for example, a phytocannabinoid (including for example, CBD) or full spectrum hemp oil in the amount of about 5.0 mg./ml. to about 1000.00 mg./ml. (based on 25% CBD conc. in the hemp oil). Unit dosage formulations of the embodiments of the present disclosure can include CBD in the amount of about 1.25 mg./ml. to about 250.00 mg./ml of the hydrogel, including a unit dose per patch or device of from about 5 mg. to about 1000 mg and a unit dose of about 5 mg., about 1000 mg or about 500 mg. Unit dosage formulations of the embodiments of the present disclosure can include full spectrum CBD oil in an amount of about 5.0 mg./ml. to about 1000.00 mg./ml (based on 25% CBD conc. in the CBD oil).

Cannabinoids, for example, CBD can have a local and/or a systemic effect and may reduce pain imparting and regulating the endocannabinoid (neurotransmitter of the nervous system) receptor activity. The subsequent body functions that may be regulated include pain, sleep, appetite and immune system response (through, at least, in part, by reducing inflammation).

For the purpose of the present disclosure, the word "cannabinoid" refers to one or more cannabinoids or cannabinoid compounds or oils or extracts from plants (for example, hemp including hemp oil and full spectrum CBD or full spectrum hemp oil) that include one or a plurality of phytocannabinoids.

Full spectrum hemp oil is oil derived from the entire hemp plant except the flower (which contains THC) and can have over 85 phytocannabinoids which can have a positive synergistic effect as compared to compositions having fewer cannabinoids. There may also be benefits to other components of it (e.g., terpenes). Such benefits and effect may include faster penetration and/or permeation of the therapeutic components thereof. Full spectrum hemp oil can include full spectrum hemp oil that has been purified to include less than the below stated amounts of one or more of the following impurities (based on the hydrogel weight):

Aflatoxins BI, 82, G1, G2 (fats, oils, lecithin, egg powder): <0.1 µg/kg of each of Aflatoxin B1, Aflatoxin B2, Aflatoxin GI and Aflatoxin G2, Sum of all positive Aflatoxins<0.4 µg/kg.

Glyphosate|AMPAiGlufosinate: <0.1 mg/kg of each of Glufosinate, Glyphosate and Aminomethylphosphonic acid (AMPA)

Mercury: <0.02 mg/kg

Arsentic: <0.03 mg/kg

Cadmium: <0.01 mg/kg

Lead: <0.05 mg/kg.

Embodiments of the present disclosure may also optionally include an effective amount of THC. Unit dosage formulations of the embodiments of the present disclosure can include THC in the amount of about 0.1 mg. to about 10 mg., about 1 mg. to about 10 mg., about 4 mg. to about 6 mg. about 5 mg. In addition to the other benefits that can be provided by other cannabinoids, THC may relieve stress and be a sleeping aid.

Menthol included in embodiments of the present disclosure (which also includes stabilized or less volatile menthol mixtures as described herein) is an active agent and an organic compound that can be made synthetically or obtained from mint oils such as corn mint and peppermint. Medicinally, it been found that menthol can have anesthetic (e.g., local) by, for example, blocking nerve signal transmission) and counterirritant properties as well as anti-inflammatory properties (e.g., systemic and local) as well as a cooling effect when administered topically to a patient. Furthermore, menthol is a vasodilator (including a topical vasodilator) that can accelerate the transport of active in the circulatory system. In general, the action of local anesthetics can restrict to the site of application and rapidly reverses upon diffusion from the site of action in the nerve. Local anesthetics can also serve an important function in providing peripheral pain relief. Topical administration of pain-relieving anesthetics can provide important advantages over systemic or local, non-topical administration. Menthol can also act as a phosphodiesterase inhibitor and calcium channel blocker (CCB). Menthol can be in an amount of about 30 wt % to about 70 wt %, about 50 wt % (wt % based on the hydrogel weight). Unit dosage formulations of the embodiments of the present disclosure can include menthol in the amount of about 0.0025 mg. to about 1000.00 mg. Unit dosage formulations of the embodiments of the present disclosure can include menthol in the amount of about 0.0025 mg./ml. to about 200 mg./ml. Unit dosage formulations of the embodiments of the present disclosure can include menthol in the amount per unit of surface area (e.g., surface areas 102 and 104 in FIG. 1, in FIG. 2A with surface areas 202 and 204 and in FIG. 2B and with surface areas 208 and 210) of about 0.0005 mg./cm$^2$ to about 1000.00 mg./cm$^2$. An effective amount of menthol includes an anesthetic, pain reducing (e.g., analgesic) or anti-inflammatory effective amount of menthol. The patch or device may include about 3 wt % of menthol in a typical about 7 cm. by about 10 cm patch (wt % based on the hydrogel weight), about 210 mg per patch or device.

Menthol may be stabilized or made less volatile using methods know in the art, such as, for example, mixing it with about 0.1 wt % to about 10 wt %, about 0.5 wt % to about 5 wt % of a surfactant including edible nonionic surfactants and ionic surfactants, such as, for example, sucrose fatty acid ester, polysorbate (e.g., polysorbate 80), hydrogenated castor oil (e.g., polyoxyethylene hydrogenated castor oil), cocamidopropyl betaine, cyclodextrins, adsorbents, encapsulations, nano-emulsions etc.

The stabilized or less volatile menthol compositions can also made by mixing together (a) menthol and (b) a menthol stabilizer compound (e.g., dissolving the menthol in the menthol stabilizer compound) in a ratio of (a) about 1 molar part menthol to (b) the amount of one or more than one of the menthol stabilizer compounds (undecylenic acid methyl ester, undecylenic acid or a salt (preferably a pharmaceutically acceptable salt) of undecylenic acid, including mixtures thereof) (i.e., one of the menthol stabilizer compounds or a mixture of more than one of the menthol stabilizer compounds) of from about 0.005 molar part to about 1.00 molar part, about 0.010 molar part to about 0.750 molar part, about 0.020 molar part to about 0.50 molar part, about 0.050 molar part to about 0.250 molar part, or about 0.10 molar part. It is believed that the menthol stabilizer compounds (e.g., undecylenic acid methyl ester and others included herein) and menthol may associate to form a menthol analog where the menthol analog's vapor pressure becomes lower than menthol itself. As a result of having a lower vapor pressure, the menthol component of the menthol analog volatizes as a lower rate than menthol by itself. Undecylenic acid methyl ester may also act as a penetration enhancer. local anesthetic, phosphodiesterase inhibitor and calcium channel blocker (CCB).

One possible explanation for the stabilization or lessening the volatility of menthol by the compound of formula (I) may be that the menthol associates with the alkenyl side chain of the menthol stabilizer compounds may provide a molecular attraction connecting the menthol stabilizer compounds and a menthol molecule, such that more than one menthol molecule may associate with a molecule of one of the menthol stabilizer compounds.

The stabilized or less volatile menthol compositions including menthol and at least one of the menthol stabilizer compounds (e.g., undecylenic acid methyl ester and others included herein) can also be made first by dissolving menthol in a pharmaceutically acceptable suitable solvent such as, for example, as a low, medium, or long chain triglyceride. Examples of such solvents are coconut oil, olive oil, palm oil, hemp oil and castor oil. Still other acceptable solvents, such as alcohols, ethers and polyalcohols, for example, propylene glycol, butylene glycol, and polyethylene glycols (PEGs) can also be used. The desired amount of at least one of the menthol stabilizer compounds disclosed herein (e.g., undecylenic acid methyl ester and others disclosed herein) is then added to that mixture. Such compositions that include menthol, solvent and one or more than one of the menthol stabilizer compounds included herein may be made where the mixture of the these ingredients includes a molar ratio of about one molar part menthol to a range of from about 0.0050 molar part to about 1.00 molar part, about 0.010 molar part to about 0.750 molar part, about 0.020 molar part to about 0.50 molar part, about 0.050 molar part to about 0.250 molar part, or about 0.10 molar part of at least one of the menthol stabilizer compounds (i.e., one of the menthol stabilizer compounds or a mixture of more than one of the menthol stabilizer compounds) included herein, preferably a molar ratio of about one molar part menthol to at most about 0.50 molar part, at most about 0.250 molar part or at most about 0.10 molar part of one or more than one of the menthol stabilizer compounds included herein. Such mixtures of menthol, solvent and menthol stabilizer compounds may be used when smaller amounts of menthol need to be stabilized (where the amount of menthol stabilizer compound to be mixed with the menthol is so small that there isn't enough of it to dissolve the menthol).

Both menthol stabilized or less volatile compositions (i.e., where the menthol is first dissolved in a solvent then added to (e.g., dissolved in) a menthol stabilizer compound included herein or where the menthol is directly dissolved in a menthol stabilizer compound included herein) can be used in orally administered and non-orally administered compositions (e.g., non-orally topically administered compositions (e.g., place on the skin or other external tissues)). However, the menthol stabilizer compounds can have a bitter taste. The dissolving of the menthol in solvent prior to the addition of at least one of the menthol stabilizer compounds included herein is preferably used in menthol containing therapeutic compositions to be administered orally because by first dissolving the menthol in a suitable solvent, less of the menthol stabilizer compounds may be used, thus lessening the bitter taste of the menthol stabilized composition and the final product in which it is included that is imparted by the menthol stabilizer compound.

The transdermal delivery systems, patches, vehicles and devices of the present disclosure can be of a suitable size and shape to fit against a body part so as to be applied to the skin surface thereof. One embodiment of the transdermal delivery systems, patches, vehicles and devices of the present disclosure include a hydrogel alone or in combination with a backing material. Examples of suitable backing material can include non-woven-fabric material, including, for example, PET/polyester, polyimide, PVC/Vinyl, silicone, acrylics, PTFE's, LDPE/HDPE, polypropylene/ethylene/etc., PVDC cotton, rayon, polyester, and blends thereof also including, for example, an acrylic PSA (pressure sensitive adhesive). The backing material can remain with the hydrogel upon application to a body part or can be a release layer that is removed subsequent to application of the embodiment to a body part. A suitable size for the hydrogel alone or in combination with a backing material or iontophoretic transdermal delivery system, patch, vehicle or device embodiments of the present disclosure, for example, is illustrated in FIG. 1 which can include the shape of a square or rectangle 100 or other polygon shape (including, e.g., triangle, pentagon, hexagon, etc.) with surface areas 102 and 104 (on opposing sides) and the dimensions of sides 106, 107, 110 and 112, each ranging in length 114, 116, 118 and 120, respectively ranging from about 2.0 cm to about 8.0 cm including each surface area ranging from about 4.0 cm$^2$ to about 64.0 cm$^2$. For example, embodiments could include patches with sides 106, 107, 110 and 112, each ranging in length 114, 116, 118 and 120, respectively, that are about 2.0 cm.×about 4.0 cm (surface area about 8.0 cm$^2$) or 8.0 cm.×about 9.0 cm (surface area about 72.0 cm$^2$).

Patch thickness 122 for hydrogels in embodiments of the present disclosure can range from about 0.10 cm to about 0.15 cm. For the iontophoretic transdermal delivery system, patch, vehicle or device embodiments of the present disclosure, patch thickness 122 can range from about 0.18 cm to about 0.22 cm. Volumes of the hydrogel components in embodiments of the present disclosure can range from about 0.10 ml to about 5.0 ml, in keeping with the above dimensions including about 2.0 ml. For example, the above referenced embodiments that include hydrogel components with a surface area 8.0 cm$^2$ based on the above ranges of thickness could have volumes ranging from about 0.50 ml to about 2.0 ml.

In the embodiments of illustrated in FIG. 1 a square would have sides 105, 107, 110 and 112 approximately equal in dimensions while a rectangle would have sides 106 and 110 approximately equal in dimensions along with sides 107 and 112 approximately equal, but the dimensions of sides 106 and 110 may not always be equal to the dimension of sides 107 and 112. In other embodiments, the dimensions of any one of sides 106, 107, 110 and 112 may be equal to the dimensions of the other sides.

Figure 2A:
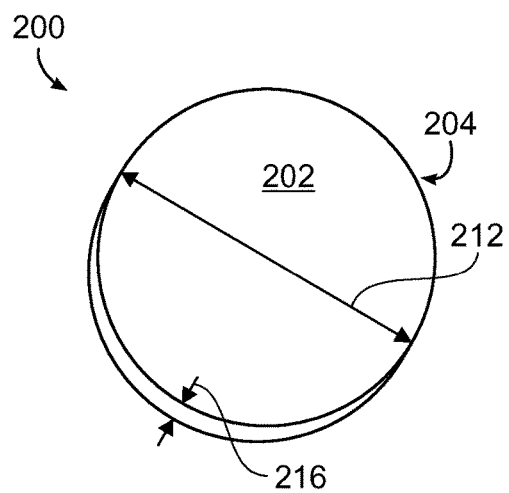
FIGS. 2A and 2B are perspective views of other embodiments of the present disclosure.
Figure 2B:
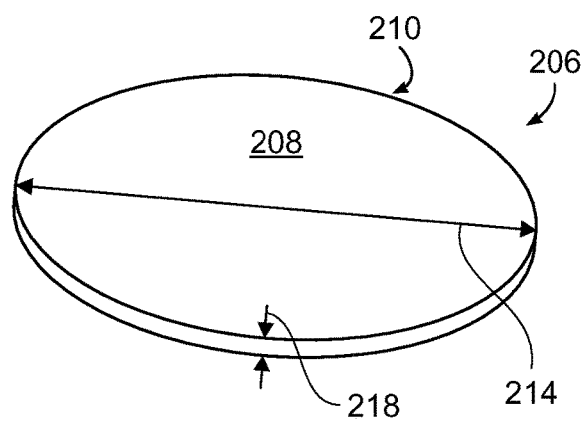

Other embodiment shapes for the hydrogel alone or in combination with a backing material or in combination with other components of the iontophoretic transdermal delivery system, patch, vehicle or device embodiments of the present disclosure can also include a circle 200 illustrated in FIG. 2A having a generally circular shape with surface areas 202 and 204 on opposing sides thereof or an ellipse 206 illustrated in FIG. 2B and with surface areas 208 and 210 on opposing sides thereof. Diameter 212 for FIG. 2A and diameter 214 for FIG. 2B can range from about 1.0 cm to about 8.0 cm including each surface area ranging from about 0.79 cm$^2$ to about 50.27 cm$^2$.

The thickness 216 for hydrogels in embodiments of the present disclosure in circle 200 in FIG. 2A and thickness 218 ellipse 206 in FIG. 2B can range from about 0.10 cm to about 0.15 cm. For the iontophoretic transdermal delivery system, patch, vehicle or device embodiments of the present disclosure, patch thickness 122 can range from about 0.18 cm to about 0.22 cm.

Unit dosage formulations of the embodiments of the present disclosure can include cannabinoid, for example, a phytocannabinoid (including for example, CBD) in the amount per unit of surface area (e.g., surface areas 102 and 104 in FIG. 1, in FIG. 2A with surface areas 202 and 204 and in FIG. 2B and with surface areas 208 and 210) of about 5.0 mg./cm$^2$ to about 1000.00 mg./cm$^2$. Unit dosage formulations of the embodiments of the present disclosure can include CBD in the amount of about 1.25 mg./cm$^2$ to about 250 mg./cm$^2$. Unit dosage formulations of the embodiments of the present disclosure can include full spectrum CBD or hemp oil in an amount of about 5.0 mg./cm$^2$ to about 1000.00 mg./cm$^2$. In one embodiment the full spectrum hemp oil is present at about 4 wt % of the hydrogel and includes a dosage of about 200 mg. An effective amount of cannabinoid includes an analgesic, pain relieving, pain treating or anti-inflammatory amount of cannabinoid.

The hydrogels (also referred to as a hydrogel reservoir or hydrogel material) used in embodiments of the present disclosure are in the form of providing a matrix for the active agents or ingredients. The hydrogels can be both natural and synthetic hydrophilic polymers may be used. Suitable hydrophilic polymers can include polyvinylpyrrolidones, polyvinyl alcohol, polyethylene oxides such as Polyox® manufactured by Union Carbide Corp.; Carbopol® manufactured by BF Goodrich of Akron, Ohio (including UV crosslinked Carbopol®); blends of polyoxyethylene or polyethylene glycols with polyacrylic acid such as Polyox® blended with Carbopol®, polyacrylamide, Klucel®, cross-linked dextran such as Sephadex (Pharmacia Fine Chemicals, AB, Uppsala, Sweden); Water Lock® (Grain Processing Corp., Muscatine, Iowa) which is a starch-graft-poly (sodium acrylate-co-acrylamide)polymer; PVP (polyvinylpyrrolidone); Gantrez™ (MVE/MA (copolymers of methyl vinyl ether (MVE) and maleic anhydride); polyvinyl alcohol; cellulose, derivatives such as hydroxyethyl cellulose, hydroxypropylmethylcellulose, low substituted hydroxypropylcellulose, and cross-linked Na-carboxymethylcellulose such as Ac-Di-Sol (FMC Corp., Philadelphia, Pa.); hydrogels such as polyhydroxyethyl methacrylate (National Patent Development Corp.); natural gums, carrageenan, alginates, xanthan, chitosan, pectin, starch, guar gum, locust bean gum, and the like, along with blends thereof.

Embodiments of the present disclosure can also include hydrogels of the present disclosure optionally having a humectant, the inclusion of which is preferable because the humectant can act as a moisturizer to keep the skin moist and keeping it from drying out, for example, glycerin, or PEG 400, or butylene glycol, or propylene glycol or the like. If we use humectants, it should be on BOTH hydrogel reservoirs (i.e., hydrogels on both electrodes). The humectant can include polyalcohols (e.g., pharmaceutically acceptable biocompatible polyalcohols), hyaluronic acid, sorbitol, honey, allantoin, etc. Pharmaceutically acceptable biocompatible polyalcohols, can include alcohols containing 2 to 10 carbon atoms and 2 to 7 hydroxyl groups including, for example, ethylene glycol, propylene glycol, butylene glycol, glycerine, glycerine betaine, erythrit (meso-1,2,3,4-Butantetrol), sorbit, mannit, methylglucoside, diglycerine, triglycerine and/or pentaerythrit as well as sodium lactate. Humectants, such as for example, glycerin can be in an amount of from about 0.50 wt % to about 10.00 wt %.

Embodiments of the present disclosure can also include hydrogels of the present disclosure optionally having an adhesive to provide better adhesion of the hydrogels of the present disclosure to the skin of the person. Examples of such adhesives can acrylics, epoxies, hydrocolloids, hydrogels, rubber based thermoplastics, polyurethanes silicones, cyanoacrylates, for example acrylic PSA (pressure sensitive adhesive).

Adhesive can be in an amount of from about 0.50 wt % to about 10.00 wt % (wt % based on the hydrogel weight) and some can also be used to make hydrogels for embodiments of the present disclosure including sodium polyacrylate, sodium CMC (carboxymethylcellulose, sodium alginate, PVP (polyvinylpyrrolidone) and Gantrez™ (MVE/MA (copolymers of methyl vinyl ether (MVE), maleic anhydride and mixtures thereof.

Figure 3A:
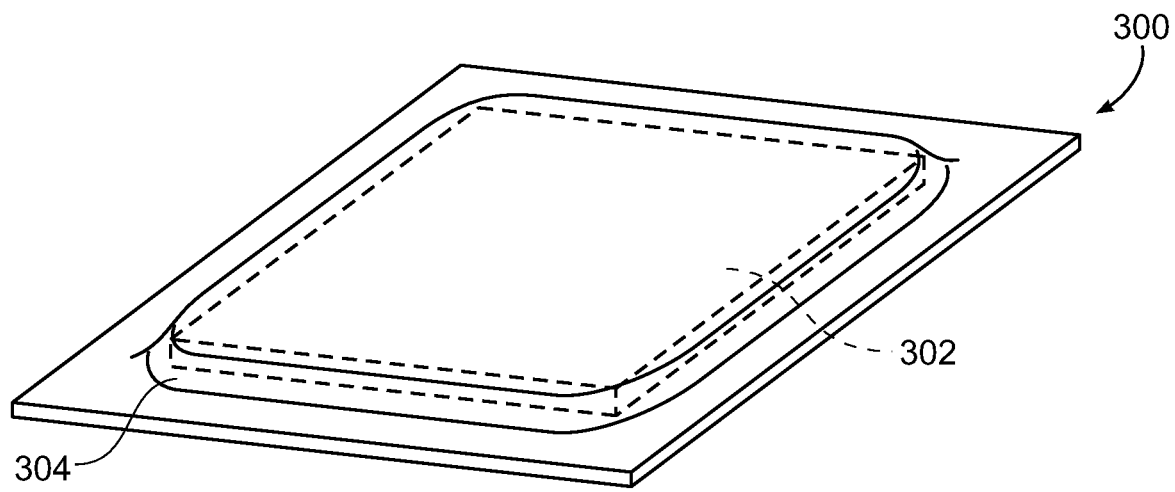
FIGS. 3A and 3B illustrate an exemplary embodiment of the present disclosure and application thereof.
Figure 3B:
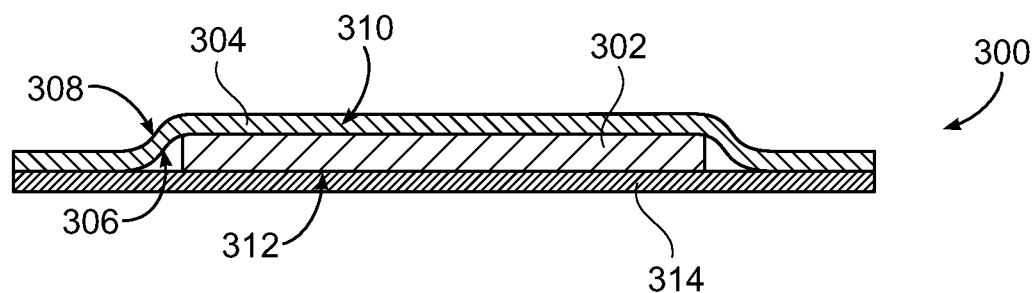

An exemplary embodiment of the present disclosure is shown in FIGS. 3A and 3B including a transdermal delivery system, patch, vehicle or device 300 which includes hydrogel containing active agent material 302 and backing material 304. The backing material 304 can be a plastic cover that is substantially resistant to moisture transport therethrough, such as, for example, PVdC—polyvinylidene chloride. The backing material 304 can have an adhesive side 306 and a side 308 that is adhesive free. The hydrogel can also optionally include an adhesive including, for example, those adhesives included in the present disclosure. The adhesive side 306 is in contact with side 310 of hydrogel containing active agent material with side 312 of the hydrogel material positioned to be against the skin 314 of the user upon application of the transdermal delivery system, patch, vehicle or device 300. Adhesive side 306 of backing material 304 is also in contact with skin 314 to adhere transdermal delivery system, patch, vehicle or device 300 to skin 314.

Figure 4A:
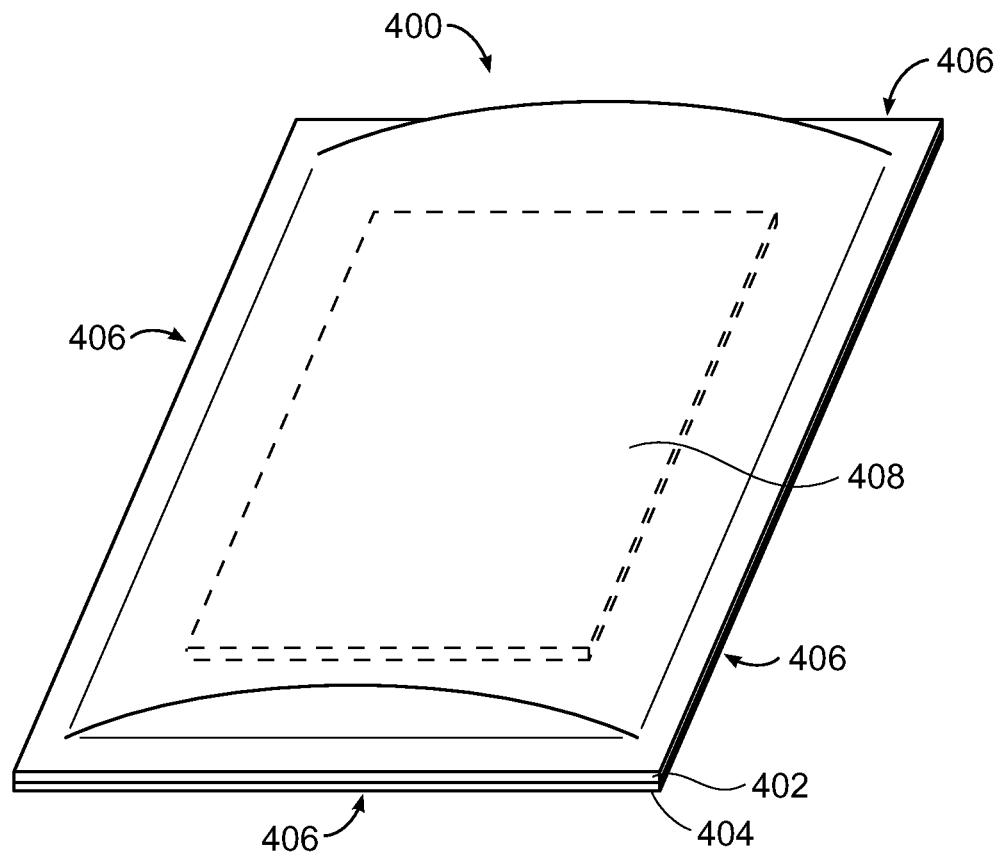
FIGS. 4A and 4B illustrate perspective and cross-sectional views of an exemplary packaging embodiment of the present disclosure.
Figure 4B:
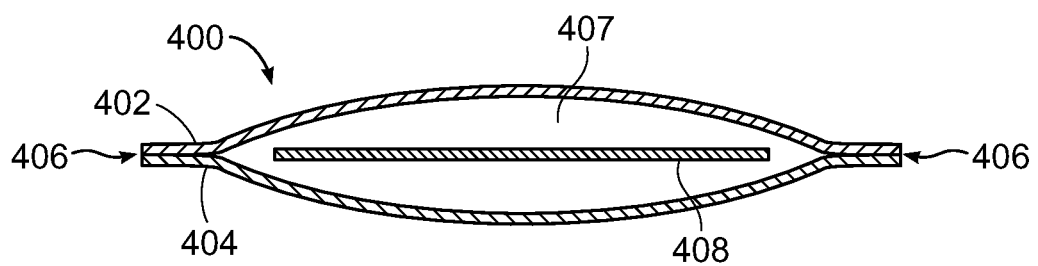

An example of a kit is a sealed water-proof package containing any of the embodiments of the present disclosure. Another aspect of the present disclosure is a water-proof package designed to contain of the composition or patch embodiments of the present disclosure and to keep a substantial amount of the moisture (i.e., water) in the embodiment. One package embodiment is illustrated in FIGS. 4A and 4B and can include an enclosure 400 (made of, for example, foil, foil laminates, HDPE (high density polyethylene) and PET (polyethylene terephthalate)) with side sections 402 and 404 that are sealed together along a common peripheral edge 406. Inside the enclosure 400 is an internal void 407 in which a transdermal delivery system, patch, vehicle or device embodiment of the present disclosure 408 is positioned.

Other embodiments of the present disclosure include a method of relieving pain and/or inflammation by topically administering and placed topically to a body part (e.g., arm, leg, knee, torso, head, neck, foot as well as those parts that make-up them), of a mammal (e.g., a human patient or veterinary patient) in need of such treatment at least one of the compositions disclosed herein. Still other embodiments of the present disclosure include a method of relieving bodily pain (local and/or systemic) by topically administering on a body part (e.g., arm, leg, knee, torso, head, neck, foot as well as those parts that make-up them), of a mammal (e.g., a human patient or veterinary patient) in need of such treatment using at least one of the compositions disclosed herein. Still other embodiments of the present disclosure include a method of relieving pain and/or inflammation (local and/or systemic) by administering to a body part, for example, placed topically on an arm, leg, knee, torso, head, neck, foot as well as those parts that make-up them, of a mammal (e.g., a human patient or veterinary patient) in need of such treatment at least one of the compositions disclosed herein. Still other embodiments of the present disclosure include a method of relieving bodily pain and/or inflammation (local and/or systemic) by topically administering to placed topically on a body part (e.g., arm, leg, knee, torso, head, neck, foot as well as those parts that make-up them), of a mammal (e.g., a human patient (i.e., person) or veterinary patient) in need of such treatment at least one of the compositions disclosed herein by placing the composition topically on a body part (e.g., arm, leg, knee, torso, head, neck, foot as well as those parts that make-up them).

Another exemplary embodiment of the present disclosure is an iontophoretic transdermal delivery system, patch, vehicle or device of the present disclosure shown in an exploded illustration in FIG. 5A and a top assembled view in FIG. 5B. The iontophoretic patch or transdermal delivery system 500 includes a top layer 502 that can be non-woven material with or without perforations thereon such as cotton, rayon, polyester, LDPE (low density polyethylene), HDPE (high density polyethylene), polypropylene and blends thereof. Iontophoretic patch or transdermal delivery system 500 also includes a circuit apparatus that includes a battery 504 and can optionally include additional electrode conductive components between battery 504 and hydrogel material 518 and 520 (e.g., hydrogel reservoirs) including, for example, two strips of conductive tape 510 and 512 and flat conductive material 514 and flat conductive material 516. For example, a first electrode can include conductive tape 510 and flat conductive material 514 and a second electrode can include conductive tape 512 and flat conductive material 516. Battery 504 includes positive terminal 506 (an anode) and negative terminal 508 (a cathode) facing toward and each terminal in contact with one of two strips of conductive tape 510 and 512, respectively, the conductive tape 510 in contact with a flat conductive material 514 and conductive tape 512 in contact with flat conductive material 516. Examples of the materials that can be used as the conductive tape include, for example, acrylics, epoxies, hydrocolloids, hydrogels, rubber based thermoplastics, polyurethanes silicones and cyanoacrylates. Side 517 of the top layer 502 should include an adhesive layer in order to secure the other components of iontophoretic patch or transdermal delivery system 500 that contact it and to provide the portion of the top layer 502 that extends beyond the peripheral sides 509, 511, 513 and 515 of the other components. The peripheral sides 501, 503, 505 and 507 of the top layer 502 should extend beyond the peripheral sides adjacent and substantially or approximately parallel thereto 509, 511, 513 and 515 of the other components such that distances 517, 521, 523 and 525 range from about 0.10 inch to about 0.50 inch, about 0.25 in.

Conductive tape 510 and conductive tape 512 can be the same material or difference materials. Examples of the materials that can be used as the conductive tape 510 and 512 include, for example, metal foil, gold, platinum, silver (e.g., various silver compounds including silver oxide, silver chloride, etc.), aluminum, copper, iron, conductive polymers, etc. Examples of the materials that can be used as the flat conductive material 514 and 516 include, for example, metal foil, gold, platinum, silver, aluminum, copper, iron, conductive polymers, etc. Flat conductive material 514 and flat conductive material 516 can be the same material or difference materials. The battery 504 should be sufficient to have 1-2 volts and 1-2 mamps (less would not allow the embodiment to work sufficiently and more would damage, e.g., burn, the skin during use). The battery 504 can be alkaline, zinc-carbon, nickel metal hydride, lithium ion, silver oxide, zinc air, lithium, nickel-cadmium. The conductive tape 510 and flat conductive material 514 are in contact with the positive terminal 506 of battery 504 (either directly or indirectly, the latter using an intervening conductor such as, for example, additional conductive tape and/or flat conductive material including conductive wire) and act as an anode and the conductive tape 512 and flat conductive material 516 are in contact with the negative terminal 508 of battery 504 (either directly or indirectly, the latter using an intervening conductor such as, for example, additional conductive tape and/or flat conductive material including conductive wire) and act as a cathode. Hydrogel material 518 and 520 are as included previously in the present disclosure and are disposed on and in contact flat conductive material 514 and 516, respectively, and positioned on the opposing sides of flat conductive material 514 and 516, respectively, to conductive tape 510 and conductive tape 512, respectively and, thereby to battery 504 and the positive terminal 506 and the negative terminal 508, thereof. The hydrogel material 518 and 520 are approximately the same lateral dimensions as the flat conductive material 514 and 516 on which they are disposed on and in contact with such that sufficient electrical power can pass from the battery to the hydrogel material 518 and 520 and complete the electrical circuit to accomplish the delivery of the active agents from the hydrogel material into the skin of a person as described in more detail below. The size of conductive tape 510 and conductive tape 512 is such that sufficient electrical power can pass from the battery to the flat conductive material 514 and 516 and hydrogel material 518 and 520 to complete the electrical circuit to accomplish the delivery of the active agents from the hydrogel material into the skin of a person as described in more detail below. There is a gap 522 that separates conductive tape 510 from conductive tape 512, flat conductive material 514 from flat conductive material 516 and hydrogel material 518 disposed on flat conductive material 514 from hydrogel material 520 disposed on flat conductive material 516.

One of the hydrogel materials 518 and 520 need to include an anionic or cationic surfactant, preferably an anionic surfactant along with the active agents (e.g., cannabinoids and menthol). As noted above, if the embodiment of the present disclosure includes a humectant, both hydrogel reservoirs will include the humectant. Because the active agents (e.g., cannabinoids and menthol) have a neutral charge, if the surfactant is anionic, the hydrogel material on the cathode side also includes the active agents (e.g., cannabinoid and menthol) to be delivered by the iontophoretic patch such that when electrical circuit is closed, the active agents migrate toward the anode and if the surfactant is cationic, the hydrogel material on the anode side also includes the active agents (e.g., cannabinoid and menthol) to be delivered by the iontophoretic patch such that when electrical circuit is closed, the active agents migrate toward the cathode.

Examples of anionic surfactants that can be used in embodiments of the present disclosure include sodium docusate (which may also act as a skin penetration enhancer as well as an ionic carrier), ammonium lauryl sulfate, sodium laureth sulfate, sodium lauryl sarcosinate, sodium myreth sulfate, sodium pareth sulfate, sodium stearte, sodium lauryl sulfate, a olefin sulfonate, and ammonium laureth sulfate). Examples of cationic surfactants that can be used in embodiments of the present disclosure include benzalkonium, benzethonium, methylbenzethonium, cetylpyridinium, alkyl-dimethyl dichlorobenzene ammonium, dequalinium and phenamylinium chlorides, cetrimonium and cethexonium bromides). Such surfactants can be in an amount of from about 1 wt % to about 10 wt % (wt % based on the hydrogel weight), about 5 wt % (wt % based on the hydrogel weight) including about 5 wt % sodium docusate (anionic) (wt % based on the hydrogel weight).

The electrical circuit is completed by placing the iontophoretic patch 500, hydrogel sides down against the skin of a person, as described above, whereby the positive side of the iontophoretic patch or transdermal delivery system 500 is electrically connected to the negative side of the iontophoretic patch 500 through the skin of the person on which it is placed. Once the circuit is complete, the electrical current pulls the hydrogel material with the active agents from the terminal where it is disposed through and into the skin of the person and toward the opposite terminal. As a result, the active agents are administered to the person at the site of the iontophoretic patch 500. For example, where the If the surfactant is anionic and the hydrogel material on the cathode side (e.g., negative terminal 508 conductive tape 512, flat conductive material 516 and hydrogel material 520) also includes the active agents along with the anionic surfactant when electrical circuit is closed, the active agents migrate through the skin toward the anode. For example, where the If the surfactant is cationic and the hydrogel material on the anode side (e.g., positive terminal 506 conductive tape 510, flat conductive material 514 and hydrogel material 518) also includes the active agents along with the cationic surfactant when electrical circuit is closed, the active agents migrate through the skin toward the cathode. Salt ions in the skin aid in completing the circuit between the anode side and the cathode side of the iontophoretic patch.

Figure 5C:
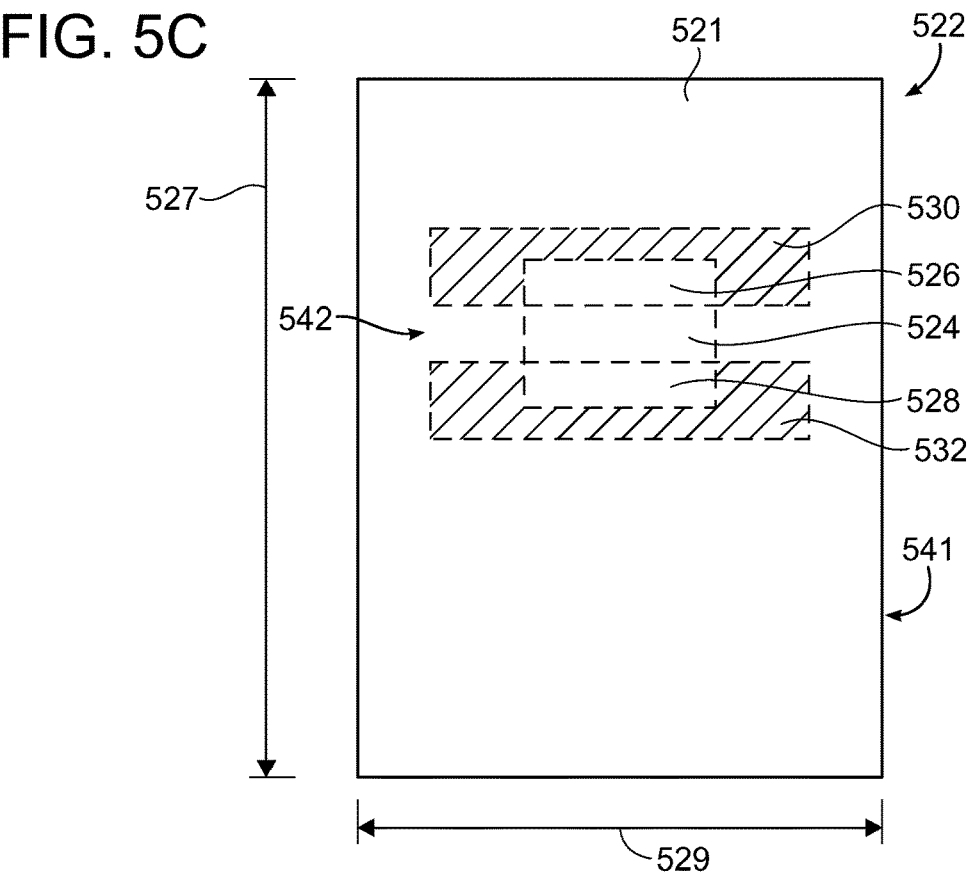
FIGS. 5C and 5D illustrate another iontophoretic embodiment of the present disclosure.
Figure 5D:
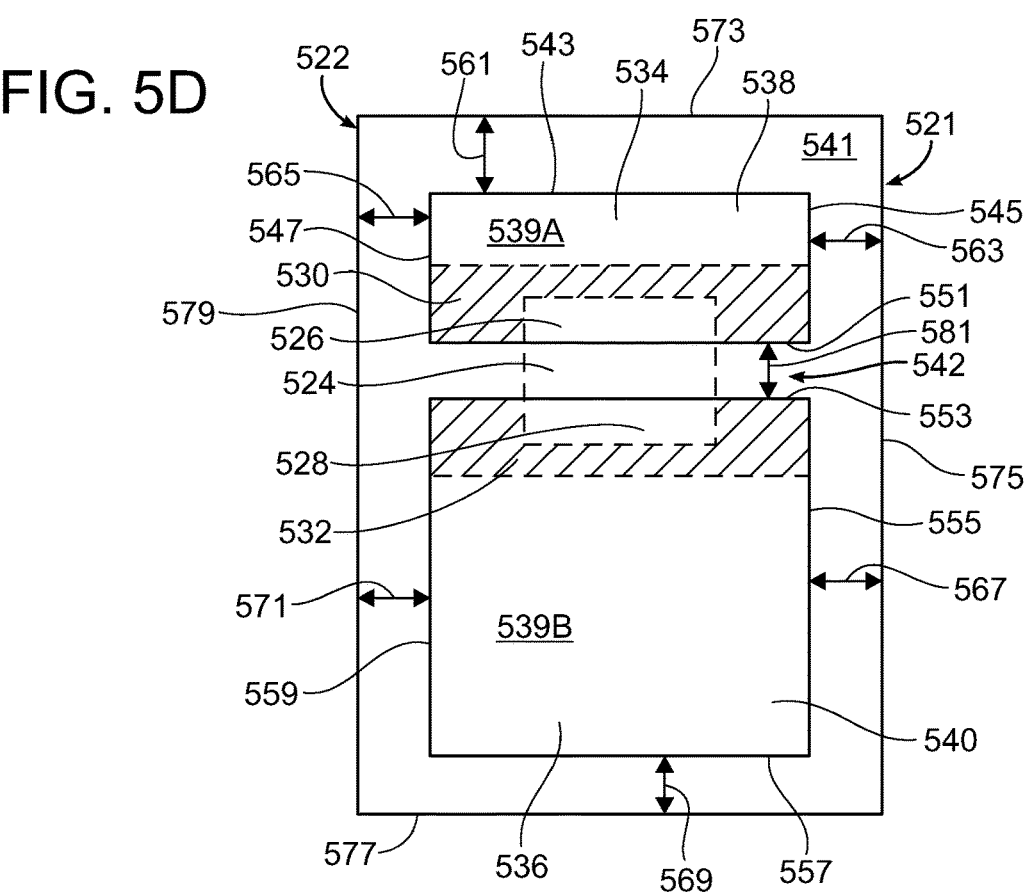

Another exemplary embodiment of the present disclosure similar in both structure and operation to the iontophoretic patch shown in FIGS. 5A and 5B is an iontophoretic transdermal delivery system, patch, vehicle or device shown in FIGS. 5C and 5D. The iontophoretic patch or transdermal delivery system 522 embodiment is illustrated in a top view of the embodiment in FIG. 5C and a bottom view of the embodiment in 5D. Iontophoretic patch 522 includes a top layer 521, a battery 524 with positive terminal 526 and negative terminal 528 facing toward and each terminal in contact with one of two strips of conductive tape 530 and 532, respectively, the conductive tape 530 in contact with a flat conductive material 534 and conductive tape 532 in contact with flat conductive material 536. The conductive tape 530 and flat conductive material 534 are in contact with the positive terminal 526 of battery 524 acts as an anode and the conductive tape 532 and flat conductive material 536 are in contact with the negative terminal 528 of battery 524 acts as a cathode. Iontophoretic patch or transdermal delivery system 522 also includes a circuit apparatus that includes a battery 524 and can optionally include additional electrode conductive components between battery 524 and hydrogel material 538 and 540 (e.g., hydrogel reservoirs) including, for example, two strips of conductive tape 530 and 532 and flat conductive material 534 and flat conductive material 536. For example, a first electrode can include conductive tape 530 and flat conductive material 534 and a second electrode can include conductive tape 532 and flat conductive material 536.

Examples of the materials that can be used as the conductive tape and flat conductive material are the same as those included for the embodiment of FIGS. 5A and 5B, Conductive tape 530 and conductive tape 532 can be the same material or difference materials. Flat conductive material 534 and flat conductive material 536 can be the same material or difference materials. Hydrogel material 538 and 540 are disposed on and in contact flat conductive material 534 and 536 on the opposing side thereof to conductive tape 530 and the conductive tape 532, respectively. There is a gap 542 that separates conductive tape 530 from conductive tape 532, flat conductive material 534 from flat conductive material 536 and hydrogel material 538 from hydrogel material 540 disposed on flat conductive material 536.

Top layer 521 has sides 573, 575, 577 and 579 with sides 575 and 579 having a length 527 that are preferably about the same and can range from about 3.5 inches to about 4.0 inches, about 3.75 inches and sides 573 and 577 having a length 529 that are preferably about the same and can range from about 3.25 inches) to about 3.75 inches), about 3.5 inches. Side 541 of the top layer 521 should include an adhesive layer in order to secure the other components of iontophoretic patch or transdermal delivery system 522.

Side 543 of flat conductive material 534 with hydrogel material and side 573 of top layer 521 should be substantially or approximately parallel to each other with a distance 561 there between that ranges from about 0.10 inch to about 0.50 inch, about 0.25 in. Side 545 of flat conductive material 534 with hydrogel material and side 575 of top layer 521 should be substantially or approximately parallel to each other with a distance 563 there between that ranges from about 0.10 inch to about 0.50 inch, about 0.25 in. Side 547 of flat conductive material 534 with hydrogel material and side 579 of top layer 521 should be substantially or approximately parallel to each other with a distance 565 there between that ranges from about 0.10 inch to about 0.50 inch, about 0.25 in. Side 555 of flat conductive material 540 with hydrogel material and side 575 of top layer 521 should be substantially or approximately parallel to each other with a distance 567 there between that ranges from about 0.10 inch to about 0.50 inch, about 0.25 in. Side 557 of flat conductive material 540 with hydrogel material and side 577 of top layer 521 should be substantially or approximately parallel to each other with a distance 569 there between that ranges from about 0.10 inch to about 0.50 inch, about 0.25 in. Side 559 of flat conductive material 540 with hydrogel material and side 579 of top layer 521 should be substantially or approximately parallel to each other with a distance 571 there between that ranges from about 0.10 inch to about 0.50 inch, about 0.25 in. Distances 561 and 569 should preferably be about the same and Distances 563, 565, 567 and 571 should preferably be about the same. Side 551 of flat conductive material 534 with hydrogel material and side 553 of flat conductive material 540 with hydrogel material should be substantially or approximately parallel to each other and gap 542 should have a distance 581 there between that ranges from about 0.08 inch to about 0.12 inch, about 0.10 inch.

The components embodiment of FIGS. 5C and 5D are similar to those in the embodiment of FIGS. 5A and 5B, one difference being that the flat conductive material and hydrogel disposed thereon for the anode is larger in area than the flat conductive material and hydrogel disposed thereon for the cathode and the active agents are disposed in the hydrogel on the anode. However, it is equally possible to arrange this embodiment where the flat conductive material 534 and other components associated therewith is the anode and the flat conductive material 536 and other components associated therewith is the cathode. Such embodiments illustrated in FIGS. 5C and 5D and included herein may also include the hydrogel with the active agents located on the flat conductive material that is larger in area to provide, for example, greater loading of the active agents into the embodiment. There is a gap 542 that separates conductive tape 530 from conductive tape 532, flat conductive material 534 from flat conductive material 536 and hydrogel material 538 disposed on flat conductive material 534 from hydrogel material 540 disposed on flat conductive material 536.

Figure 5E:
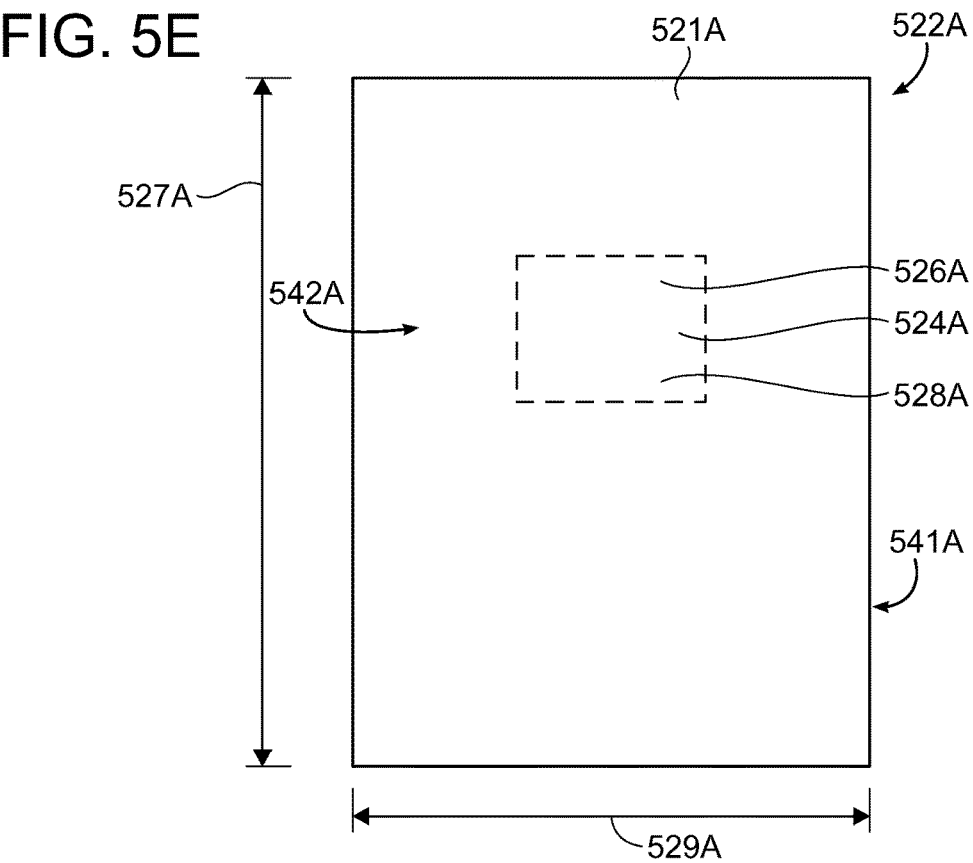
FIGS. 5E and 5F illustrate another iontophoretic embodiment of the present disclosure.
Figure 5F:
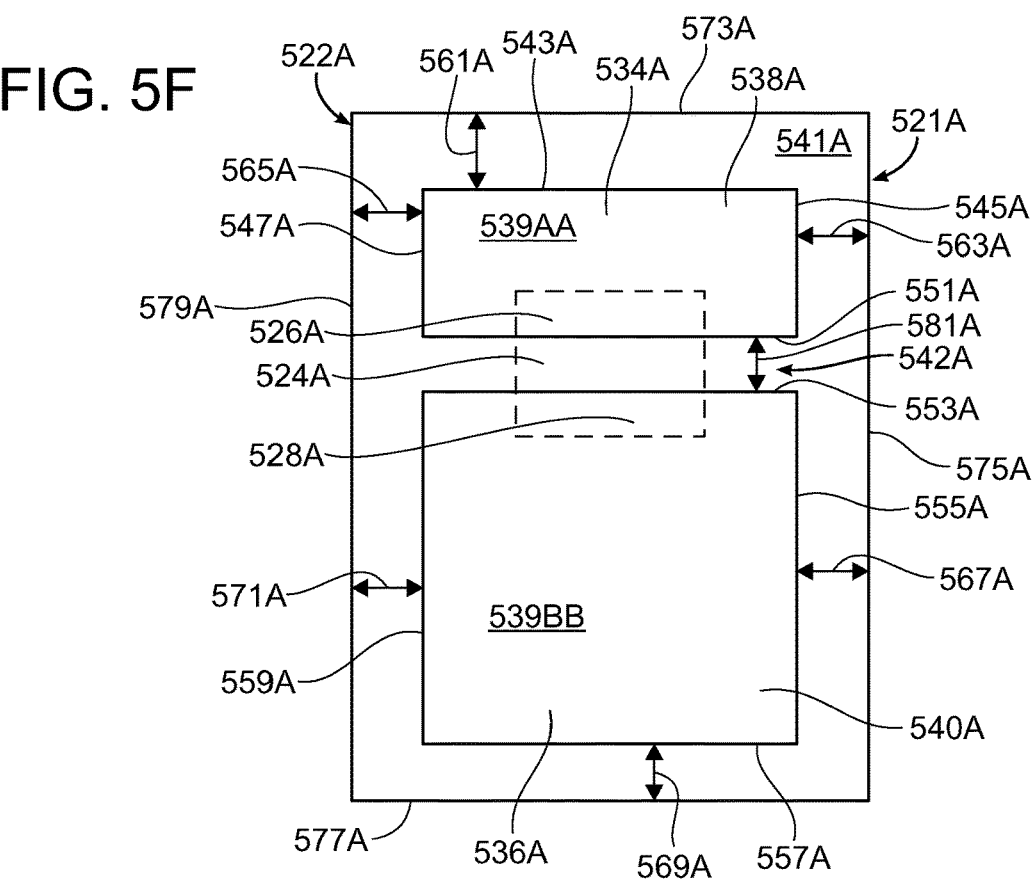

Another exemplary embodiment of the present disclosure similar in both structure and operation to the iontophoretic patch shown in FIGS. 5A and 5B and the iontophoretic patch shown in FIGS. 5C and 5D is an iontophoretic transdermal delivery system, patch, vehicle or device shown in FIGS. 5E and 5F. The iontophoretic patch or transdermal delivery system 522A embodiment is illustrated in a top view of the embodiment in FIG. 5E and a bottom view of the embodiment in 5F. Iontophoretic patch 522A includes a top layer 521A, a battery 524 A with positive terminal 526A and negative terminal 528A facing toward and each terminal in contact with one of two flat conductive material 534A and flat conductive material 536A, respectively. The flat conductive material 534A are in contact with the positive terminal 526A of battery 524A acts as an anode and the flat conductive material 536A are in contact with the negative terminal 528A of battery 524A acts as a cathode. Iontophoretic patch or transdermal delivery system 522A also includes a circuit apparatus that includes a battery 524A and can optionally include additional electrode conductive components between battery 524A and hydrogel material 538A and 540A (e.g., hydrogel reservoirs) including, for example, flat conductive material 534A and flat conductive material 536A. For example, a first electrode can include flat conductive material 534A and a second electrode can include flat conductive material 536A. Examples of the materials that can be used as the flat conductive material are the same as those included for the embodiment of FIGS. 5A and 5B, Flat conductive material 534A and flat conductive material 536A can be the same material or difference materials. Hydrogel material 538A and 540A are disposed on and in contact flat conductive material 534A and 536A on the opposing side to the battery 524A. There is a gap 542A that separates flat conductive material 534A from flat conductive material 536A and hydrogel material 538A from hydrogel material 540A disposed on flat conductive material 536.

Top layer 521A has sides 573A, 575A, 577A and 579A with sides 575A and 579A having a length 527A that are preferably about the same and can range from about 3.5 inches to about 4.0 inches, about 3.75 inches 3.5 in. and sides 573A and 577A having a length 529A that are preferably about the same and can range from about 3.25 inches) to about 3.75 inches), about 3.5 inches. Side 541A of the top layer 521A should include an adhesive layer in order to secure the other components of iontophoretic patch or transdermal delivery system 522A.

Side 543A of flat conductive material 534A with hydrogel material and side 573A of top layer 521A should be substantially or approximately parallel to each other with a distance 561A there between that ranges from about 0.10 inch to about 0.50 inch, about 0.25 in. Side 545A of flat conductive material 534A with hydrogel material and side 575A of top layer 521A should be substantially or approximately parallel to each other with a distance 563A there between that ranges from about 0.10 inch to about 0.50 inch, about 0.25 in. Side 547A of flat conductive material 534A with hydrogel material and side 579A of top layer 521A should be substantially or approximately parallel to each other with a distance 565A there between that ranges from about 0.10 inch to about 0.50 inch, about 0.25 in. Side 555A of flat conductive material 540A with hydrogel material and side 575A of top layer 521A should be substantially or approximately parallel to each other with a distance 567A there between that ranges from about 0.10 inch to about 0.50 inch, about 0.25 in. Side 557A of flat conductive material 540A with hydrogel material and side 577A of top layer 521A should be substantially or approximately parallel to each other with a distance 569A there between that ranges from about 0.10 inch to about 0.50 inch, about 0.25 in. Side 559A of flat conductive material 540A with hydrogel material and side 579A of top layer 521A should be substantially or approximately parallel to each other with a distance 571A there between that ranges from about 0.10 inch to about 0.50, about 0.25 in. Distances 561A and 569A should preferably be about the same and Distances 563A, 565A, 567A and 571A should preferably be about the same. Side 552A of flat conductive material 534 with hydrogel material and side 553A of flat conductive material 540A with hydrogel material should be substantially or approximately parallel to each other and gap 542A should have a distance 581A there between that ranges from about 0.08 inch to about 0.12 inch, about 0.10 inch.

The components embodiment of FIGS. 5E and 5F are similar to those in the embodiment of FIGS. 5A and 5B and the embodiment of FIGS. 5C and 5D, one difference being that the flat conductive material and hydrogel disposed thereon for the anode is larger in area than the flat conductive material and hydrogel disposed thereon for the cathode and the active agents are disposed in the hydrogel on the anode. However, it is equally possible to arrange this embodiment where the flat conductive material 534A and other components associated therewith is the anode and the flat conductive material 536A and other components associated therewith is the cathode. Such embodiments illustrated in FIGS. 5E and 5F and included herein may also include the hydrogel with the active agents located on the flat conductive material that is larger in area to provide, for example, greater loading of the active agents into the embodiment. There is a gap 542A that separates flat conductive material 534A from flat conductive material 536A and hydrogel material 538A disposed on flat conductive material 534A from hydrogel material 540A disposed on flat conductive material 536A.

Figure 6E:
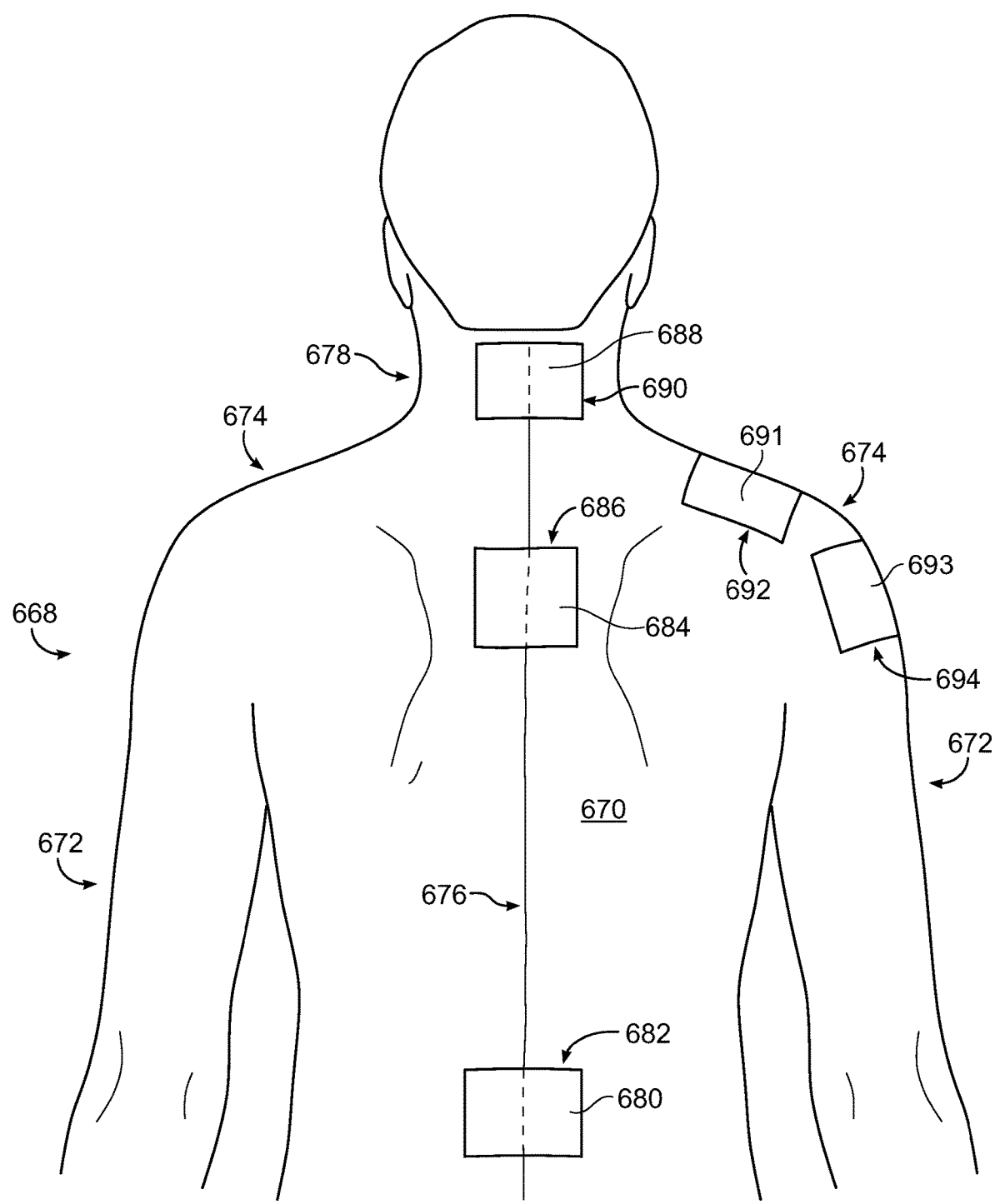

Embodiments of the present disclosure are intended to be placed on the skin surface of a body part or body parts or portions thereof where a person is experiencing pain and/or inflammation resulting from, for example, injury or other physical diseases, stresses or conditions. Non-limiting exemplary embodiments showing possible placement are illustrated in FIGS. 6A to 6F. FIGS. 6A and 6B show a top view and side view, respectively, of an arm 600 including a hand 602, wrist 604, forearm 606, elbow area 607 and upper arm 608. One of the embodiments of the present disclosure 610 can be positioned against the hand 602 at 612. An alternative is an embodiment of the present disclosure 614 can be positioned against the wrist 604 at 616. An alternative is an embodiment of the present disclosure 618 can be positioned against the forearm 606 at 620. An alternative is an embodiment of the present disclosure 619 can be positioned against the lower part of the forearm 606 at 621. An alternative is an embodiment of the present disclosure 622 can be positioned against the elbow area 607 at 624. An alternative is an embodiment of the present disclosure 626 can be positioned against the upper arm 608 at 628.

FIGS. 6C and 6D show a side view and front view, respectively, of a leg 630 including a foot 632, ankle area 634, calf 636, knee area 638 and upper leg 640. One of the embodiments of the present disclosure 642 can be positioned against the front of the ankle area 634 at 644. An alternative is an embodiment of the present disclosure 646 can be positioned against the side of the ankle area 634 at 648. An alternative is an embodiment of the present disclosure 650 can be positioned against the back of the ankle area 634 (e.g., against the Achilles tendon) at 652. An alternative is an embodiment of the present disclosure 654 can be positioned against the side of the back of the calf 636 at 656. An alternative is an embodiment of the present disclosure 658 can be positioned against the knee area 638 at 660. An alternative is an embodiment of the present disclosure 662 can be positioned against the front of the upper leg 640 at 664.

FIG. 6E shows a rear view of an upper torso 668 including back 670, arms 672, shoulder area 674, spinal/backbone area 676 and neck 678. One of the embodiments of the present disclosure 680 can be positioned against the lower region of the back 670 adjacent the spinal/backbone area 676 at 682. An alternative is an embodiment of the present disclosure 684 can be positioned against the upper region of the back 670 adjacent the spinal/backbone area 676 at 686. An alternative is an embodiment of the present disclosure 688 can be positioned against the back of the neck 678 (e.g., against the spinal/backbone area 676) at 690. An alternative is an embodiment of the present disclosure 691 can be positioned against the upper area of the shoulder area 674 at 692. An alternative is an embodiment of the present disclosure 693 can be positioned against the lower area of the shoulder area 674 at 694.

Figure 6F:
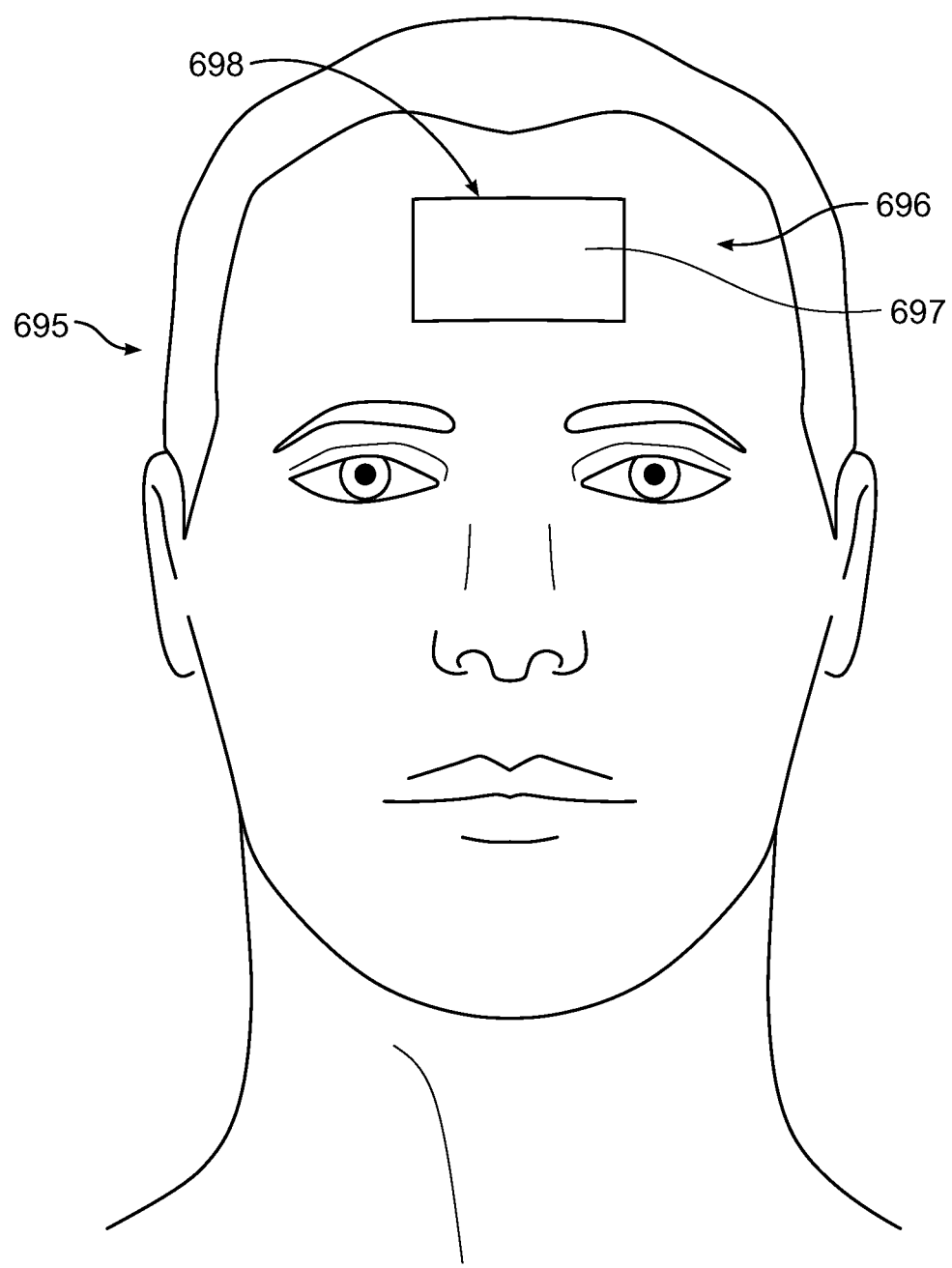

FIG. 6F shows a front view of a head 695 including a forehead 696. One of the embodiments of the present disclosure 697 can be positioned against the forehead 696 at 698.

Although all surfaces of the embodiments of the present disclosure can be applied to the skin surface of body parts or portions thereof to administer the agents included therein (e.g., CBD and menthol) for transdermal delivery into and through the tissues of the skin surface to bring about the intended local and/or systemic effect, the largest surfaces (e.g., surface areas 102 and 104 in FIG. 1, in FIG. 2A with surface areas 202 and 204 and in FIG. 2B and with surface areas 208 and 210, the exposed side 519A of hydrogel material 518 and the exposed side 519B of hydrogel material 520 in FIGS. 5A and 5B, the exposed side 539A of Hydrogel material 538 and the exposed side 539B of hydrogel material 540 in FIGS. 5C and 5D, the exposed side 539AA of Hydrogel material 538A and the exposed side 539BB of hydrogel material 540A in FIGS. 5E and 5F) should preferably be placed against those skin surfaces including the embodiments of FIGS. 6A to 6F.

For embodiments that are hydrogel embodiments placed on a body part (e.g., patch embodiments and not an iontophoretic patch), the dosing time can range from about 30 minutes to about 12 hours, about 30 minutes to about 8 hours (based on in vitro testing), 30 minutes to about 2 hours or about 30 minutes to about 1 hour. For embodiments that are hydrogel iontophoretic embodiments placed on a body part, the dosing time can range from about 30 minutes to about 12 hours, about 30 minutes to about 8 hours (based on in vitro testing), 30 minutes to about 2 hours or about 30 minutes to about 1 hour.

Figure 7A:
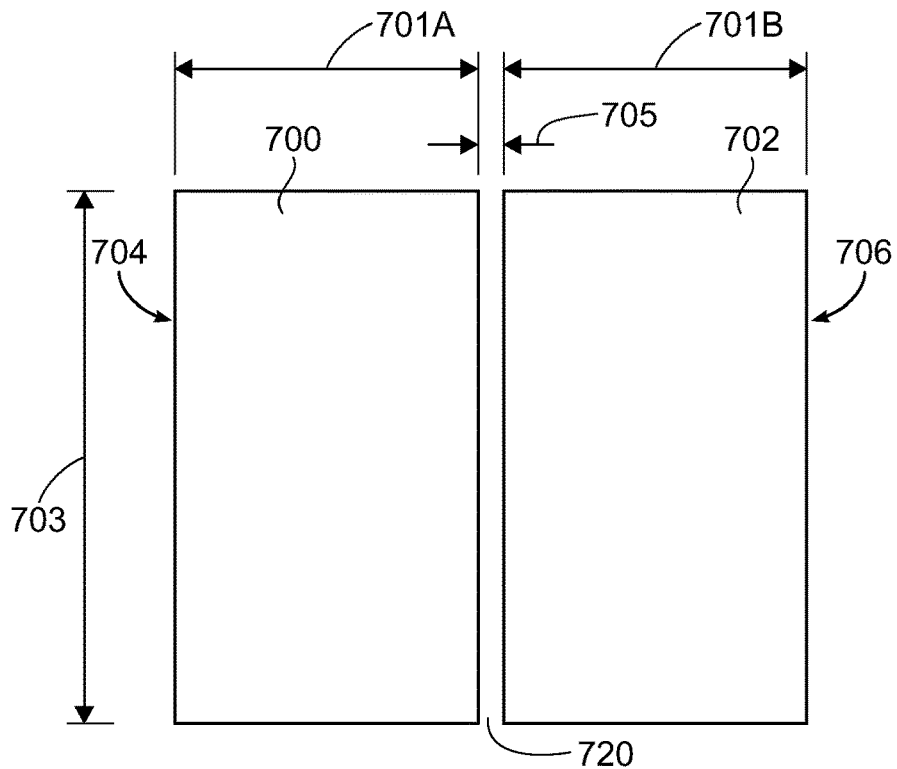
FIGS. 7A to 7D illustrate an exemplary embodiment of the present disclosure and assembly thereof.
Figure 7B:
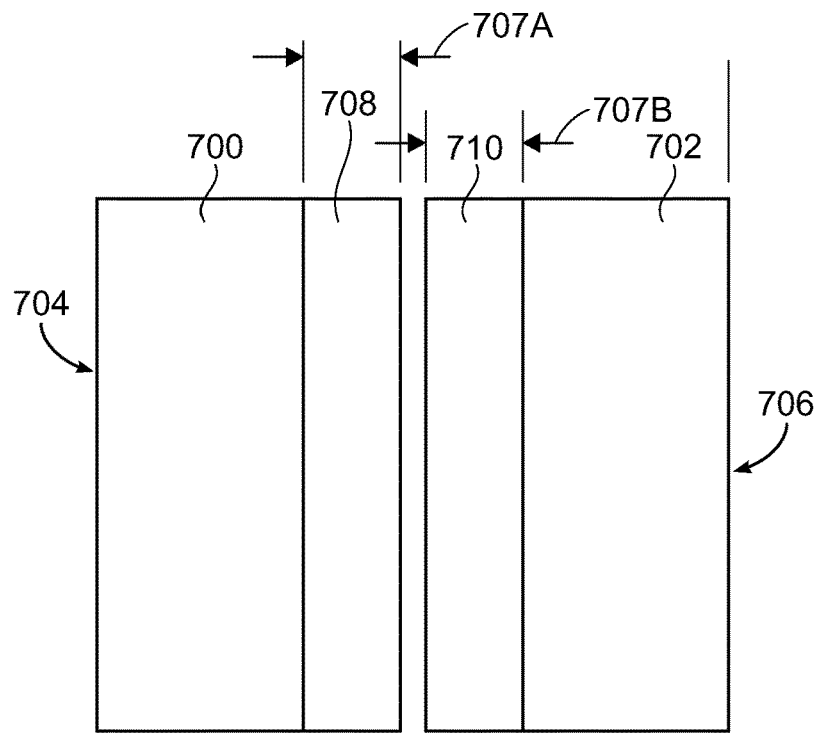
Figure 7C:
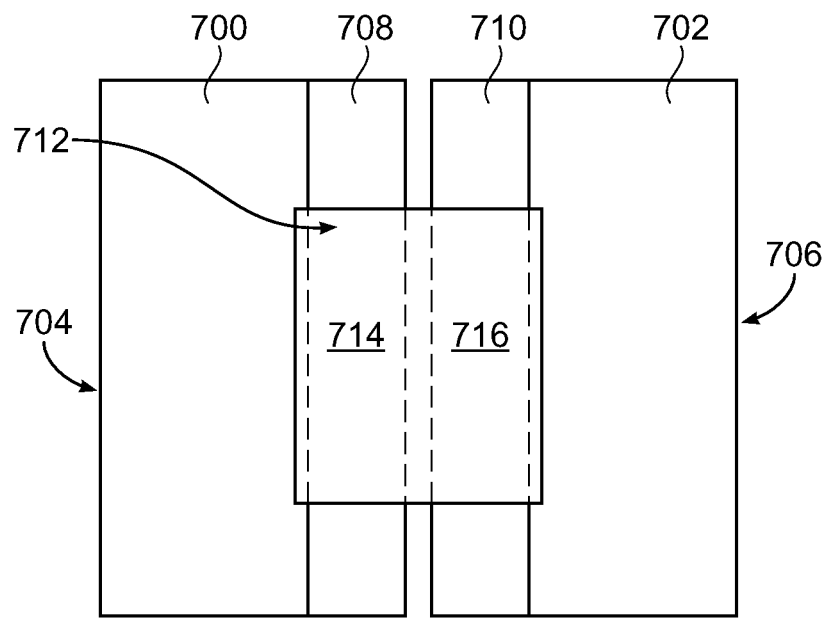
Figure 7D:
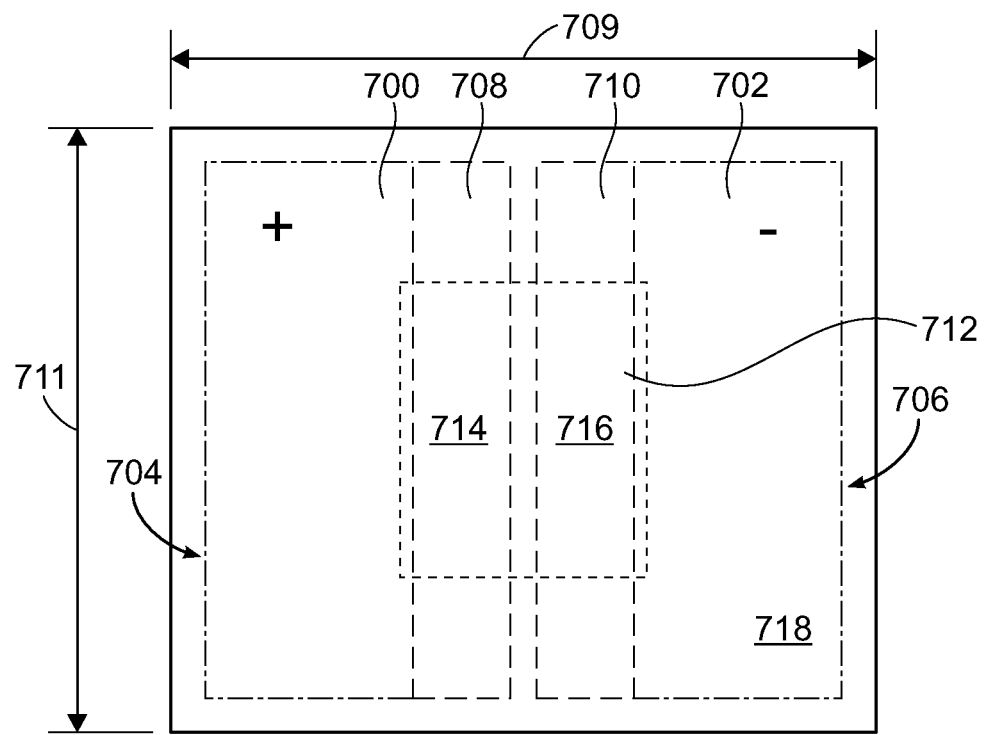

Any standard manufacturing procedure known in the art may be used to manufacture the transdermal delivery system, patch, vehicle or device of the present disclosure. An exemplary manufacturing process that can be used to manufacture the hydrogel iontophoretic patch or transdermal delivery system embodiments of the present disclosure is illustrated in FIGS. 7A-7D. Exemplary dimensions of the embodiment of FIGS. 5A and 5B with the overall dimensions thereof applicable to the embodiment of FIGS. 5C and 5D also included in FIGS. 7A-7D. In FIG. 7A, flat conductive material 700 and flat conductive material 702 (with width dimensions 701A and 701B being from about 1.0 inch to about 2.0 inches or about 1.56625 inches and each with a length dimension 703 that is about the same being from about 2.5 inches to about 3.0 inches or about 2.75 inches) and gap 720 therebetween (with a dimension 705 being from about 0.10 inch to about 0.15 inch or about 0.125 inches) are laminated with hydrogel material 704 and 706, respectively with hydrogel material 704 and hydrogel material 706 have width and length dimensions approximately the same as those of flat conductive material 700 and flat conductive material 702 or slightly smaller in one of both dimensions. Next, as shown in FIG. 7B, conductive tape 708 is disposed on flat conductive material 700 on the opposing side to hydrogel material 704 and conductive tape 710 is disposed on flat conductive material 702 on the opposing side to hydrogel material 706. Conductive tape 708 and conductive tape 710 with length dimensions approximately the same as the length dimensions 703A and 703B and width dimension 707A and 707B being from about 0.40 inch to about 0.60 inch or about 0.50 inches Next, as shown in FIG. 7C, battery 712 is disposed so that the positive terminal thereof 714 is positioned in contact with conductive tape 708 and negative terminal thereof 716 is positioned in contact with conductive tape 710. Next, as shown in FIG. 7D, top layer 718 is disposed on top of the side with flat conductive material 700, flat conductive material 702, conductive tape 708, conductive tape 710 and battery 712 and can optionally be marked to identify the positive side of the hydrogel iontophoretic patch and the negative side of the hydrogel iontophoretic patch (with a width dimension 709 being from about 3.40 inches to about 3.60 inches or about 3.75 inches and a length dimension 711 being from about 2.75 inches to about 3.50 inches or about 3.25 inches.

The embodiments of the present disclosure may also include a rate-controlling membrane on the skin surface side of the transdermal delivery system, patch, vehicle or device of the present disclosure. The materials used to form such a membrane are selected to limit the flux of one or more components contained in the drug formulation, and the membrane may be either microporous or dense. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, polysiloxane-polycarbonate block copolymer and the like.

Example 1

TABLE 1

| Item# | Ingredients | Function | w/w % Example amount (about) | Lower limit w/w % (about) | Upper limit w/w % (about) |
|---|---|---|---|---|---|
| 1 | Hemp Oil (CBD, THC etc) | API or cosmetic | 35 | 25 | 65 |
| 2 | Undecylenic Acid methyl ester | Menthol stabilizer | 9.5 | 0.50 | 20 |
| 3 | Menthol | API | 50 | 30 | 70 |

TABLE 1-continued

| Item# | Ingredients | Function | w/w % Example amount (about) | Lower limit w/w % (about) | Upper limit w/w % (about) |
|---|---|---|---|---|---|
| 4 | Sodium docusate | Surfactant and ionic potential | 5 | 1 | 10 |
| 5 | DMSO | Penetration enhancer | 0.5 | 0.001 | 5.0 |

The above ingredients in Table 1 are prepared by add the menthol to the undecylenic acid methyl ester to form a pre-formed mixture of a stabilized menthol composition. The hemp oil and sodium docusate are then added to the pre-formed mixture of the stabilized menthol composition to form a concentrate composition. The concentrate composition can then be loaded into a hydrogel material at from between about 1 wt % to about 30 wt % by weight of the hydrogel material (UV crosslinked Carbopol®), the latter also including a skin adhesive. The final concentration in the hydrogel material is as follows: about 90 wt % skin adhesive, about 5 wt % menthol, about 4 wt % hemp oil and about 0.95% wt % undecylenic acid methyl ester, and 0.05% wt % DMSO, added together to a total of 100 wt %.

Example 2

The hydrogel of Example 1 included in the embodiment of FIGS. 5C and 5D in hydrogel reservoir or material 538 and hydrogel reservoir or material 540 only the UV crosslinked Carbopol® with a battery having about 10 mAH @ about 1-2 mA current; top layer 521—non-woven polyester material with acrylic PSA (adhesive); conductive tape 530 and 532 and flat conductive material 534 and flat conductive material 536 are a silver compound; and the thickness of the device is about 0.20 cm. Top layer 521 has sides 573, 575, 577 and 579 with sides 575 and 579 having a length 527 that are preferably about the same and can range from about 3.5 inches to about 4.0 inches, about 3.75 inches 3.5 in. and sides 573 and 577 having a length 529 that are preferably about the same and can range from about 3.25 inches) to about 3.75 inches), about 3.5 inches. Gap 542 has a length about 2.75 inches. Side 543 of flat conductive material 534 with hydrogel material and side 573 of top layer 521 should be substantially or approximately parallel to each other with a distance 561 therebetween of about 0.25 in. Side 545 of flat conductive material 534 with hydrogel material and side 575 of top layer 521 should be substantially or approximately parallel to each other with a distance 567 therebetween of about 0.25 in. Side 547 of flat conductive material 534 with hydrogel material and side 579 of top layer 521 should be substantially or approximately parallel to each other with a distance 565 therebetween of about 0.25 in. Side 555 of flat conductive material 540 with hydrogel material and side 575 of top layer 521 should be substantially or approximately parallel to each other with a distance 567 therebetween of about 0.25 in. Side 557 of flat conductive material 540 with hydrogel material and side 577 of top layer 521 should be substantially or approximately parallel to each other with a distance 569 therebetween of about 0.25 in. Side 559 of flat conductive material 540 with hydrogel material and side 579 of top layer 521 should be substantially or approximately parallel to each other with a distance 571 therebetween of about 0.25 in. Distances 561 and 569 should preferably be about the same and Distances 563, 565, 567 and 571 should preferably be about the same. Side 552 of flat conductive material 534 with hydrogel material and side 553 of flat conductive material 540 with hydrogel material should be substantially or approximately parallel to each other and gap 542 should have a distance 581 therebetween of about 0.10 inch.

All publications, including but not limited to, issued patents, patent applications, and journal articles, cited in this application are each herein incorporated by reference in their entirety.

Thus, while there have been shown, described and pointed out, fundamental novel features of the present disclosure as applied to the exemplary embodiments thereof, it will be understood that various omissions and substitutions and changes in the form and details of devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

This written description uses examples as part of the disclosure, including the best mode, and also to enable any person skilled in the art to practice the disclosed implementations, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

While there have been shown, described and pointed out, fundamental features of the present disclosure as applied to the exemplary embodiments thereof, it will be understood that various omissions and substitutions and changes in the form and details of compositions, devices and methods illustrated, and in their operation, may be made by those skilled in the art without departing from the spirit or scope of the present disclosure. Moreover, it is expressly intended that all combinations of those elements and/or method steps, which perform substantially the same function in substantially the same way to achieve the same results, are within the scope of the present disclosure. Moreover, it should be recognized that structures and/or elements and/or method steps shown and/or described in connection with any disclosed form or embodiment of the present disclosure may be incorporated in any other disclosed or described or suggested form or embodiment as a general matter of design choice. It is the intention, therefore, to be limited only as indicated by the scope of the claims appended hereto.

The invention claimed is:

1. A transdermal delivery system, comprising:
    a first hydrogel reservoir and a second hydrogel reservoir separated from each other, one of the first hydrogel reservoir and the second hydrogel reservoir including a mixture of an anionic or cationic surfactant, DMSO and at least one cannabinoid, and a stabilized menthol composition for lowering the rate of volatilization of menthol, the stabilized menthol composition including a pre-formed mixture consisting essentially of menthol and a menthol stabilizer compound including undecylenic acid methyl ester wherein the stabilized menthol composition is formed and encapsulated in a cyclodextrin prior to being added to the mixture of the anionic or cationic surfactant, DMSO and the at least one cannabinoid; and
    a circuit apparatus including a power source, the circuit apparatus configured to supply power to the first hydrogel reservoir and the second hydrogel reservoir.

2. The transdermal delivery system of claim 1, wherein the circuit apparatus further includes a first electrode interposed between the first hydrogel reservoir and the power source and a second electrode interposed between the second hydrogel reservoir and the power source, for conducting power between the power source and the first and second hydrogel reservoirs.

3. The transdermal delivery system of claim 1, wherein said first hydrogel reservoir includes an anionic surfactant, said at least one cannabinoid and said stabilized menthol composition.

4. The transdermal delivery system of claim 1, wherein said first hydrogel reservoir includes a cationic surfactant, said at least one cannabinoid and said stabilized menthol composition.

5. The transdermal delivery system of claim 2, wherein said first hydrogel reservoir includes an anionic surfactant, the power source includes an anode and a cathode and said first electrode is in contact with said cathode, said second electrode is in contact with said anode and said first hydrogel reservoir includes said at least one cannabinoid and said stabilized menthol composition.

6. The transdermal delivery system of claim 2, wherein said first hydrogel reservoir includes a cationic surfactant, the power source includes an anode and a cathode and said first electrode is in contact with said anode, said second electrode is in contact with said cathode and said first hydrogel reservoir includes said at least one cannabinoid and said stabilized menthol composition.

7. The transdermal delivery system of claim 2, wherein said first electrode and said second electrode each include a conductive material.

8. A transdermal delivery system, comprising:
    a first hydrogel reservoir and a second hydrogel reservoir separated from each other, one of the first hydrogel reservoir and the second hydrogel reservoir including a mixture of an anionic or cationic surfactant, DMSO and a full spectrum hemp oil, and a stabilized menthol composition for lowering the rate of volatilization of menthol, the stabilized menthol composition including a pre-formed mixture consisting essentially of menthol and a menthol stabilizer compound including undecylenic acid methyl ester wherein the stabilized menthol composition is formed and encapsulated in a cyclodextrin prior to being added to the mixture of the anionic or cationic surfactant, DMSO and the full spectrum hemp oil; and
    a circuit apparatus including a power source, the circuit apparatus configured to supply power to the first hydrogel reservoir and the second hydrogel reservoir,
    wherein the transdermal delivery system includes less than 0.3% THC and the full spectrum hemp oil is purified to include the below stated amounts of one or more of the following impurities:

less than 0.1 µg/kg of each of Aflatoxins BI, 82, G1, G2 and the sum of all positive Aflatoxins is less than 0.4 µg/kg;

less than 0.1 mg/kg of each of Glufosinate, Glyphosate and Aminomethylphosphonic acid (AMPA);

less than 0.02 mg/kg of mercury;

less than 0.03 mg/kg of arsenic;

less than 0.01 mg/kg of cadmium; and less than 0.05 mg/kg of lead.

9. The transdermal delivery system of claim 8, wherein the circuit apparatus further includes a first electrode interposed between the first hydrogel reservoir and the power source and a second electrode interposed between the second hydrogel reservoir and the power source, for conducting power between the power source and the first and second hydrogel reservoirs.

10. The transdermal delivery system of claim 8, wherein said first hydrogel reservoir includes an anionic surfactant, said full spectrum hemp oil and said stabilized menthol composition.

11. The transdermal delivery system of claim 8, wherein said first hydrogel reservoir includes a cationic surfactant, said full spectrum hemp oil and said stabilized menthol composition.

12. The transdermal delivery system of claim 9, wherein said first hydrogel reservoir includes an anionic surfactant, the power source includes an anode and a cathode and said first electrode is in contact with said cathode, said second electrode is in contact with said anode and said first hydrogel reservoir includes said full spectrum hemp oil and said stabilized menthol composition.

13. The transdermal delivery system of claim 9, wherein said first hydrogel reservoir includes a cationic surfactant, the power source includes an anode and a cathode and said first electrode is in contact with said anode, said second electrode is in contact with said cathode and said first hydrogel reservoir includes said full spectrum hemp oil and said stabilized menthol composition.

14. The transdermal delivery system of claim 9, wherein said first electrode and said second electrode each include a conductive material.

15. A method of treating pain or inflammation in a body part or portion thereof of a mammal using a transdermal delivery system, the transdermal delivery system comprising:

a first hydrogel reservoir and a second hydrogel reservoir separated from each other, one of the first hydrogel reservoir and the second hydrogel reservoir including a mixture of an anionic or cationic surfactant, DMSO and at least one cannabinoid, and a stabilized menthol composition for lowering the rate of volatilization of menthol, the stabilized menthol composition including a pre-formed mixture consisting essentially of menthol and a menthol stabilizer compound including undecylenic acid methyl ester wherein the stabilized menthol composition is formed and encapsulated in a cyclodextrin prior to being added to the mixture of the anionic or cationic surfactant, DMSO and the at least one cannabinoid; and a circuit apparatus including a power source, the circuit apparatus configured to supply power to the first hydrogel reservoir and the second hydrogel reservoir, the method comprising:

topically applying the said first hydrogel reservoir and said second hydrogel reservoir to a skin surface of the body part of the mammal and thereby completing an electrical circuit through the skin of the mammal between said first hydrogel reservoir and said second hydrogel reservoir using said power source.

16. The method of claim 15, wherein the circuit apparatus further includes a first electrode interposed between the first hydrogel reservoir and the power source and a second electrode interposed between the second hydrogel reservoir and the power source, for conducting power between the power source and the first and second hydrogel reservoirs.

17. The method of claim 15, wherein said first hydrogel reservoir includes an anionic surfactant.

18. The method of claim 15, wherein said first hydrogel reservoir includes a cationic surfactant.

19. The method of claim 16, wherein said first hydrogel reservoir includes an anionic surfactant, the power source includes an anode and a cathode and said first electrode is in contact with said cathode, said second electrode is in contact with said anode and said first hydrogel reservoir includes said at least one cannabinoid and a stabilized menthol composition.

20. The method of claim 16, wherein said first hydrogel reservoir includes a cationic surfactant, the power source includes an anode and a cathode and said first electrode is in contact with said anode, said second electrode is in contact with said cathode and said first hydrogel reservoir includes said at least one cannabinoid and said stabilized menthol composition.

* * * * *